(12) United States Patent
Tan

(10) Patent No.: US 8,282,636 B2
(45) Date of Patent: Oct. 9, 2012

(54) ORTHOPEDIC EXTERNAL FIXATOR AND METHOD OF USE

(75) Inventor: Virak Tan, Murray Hill, NJ (US)

(73) Assignee: IMDS Corporation, Logan, UT (US)

( * ) Notice: Subject to any disclaimer, the term of this patent is extended or adjusted under 35 U.S.C. 154(b) by 258 days.

(21) Appl. No.: 12/462,807

(22) Filed: Aug. 10, 2009

(65) Prior Publication Data

US 2011/0034924 A1 Feb. 10, 2011

(51) Int. Cl.
*A61B 17/00* (2006.01)

(52) U.S. Cl. ........................................................ 606/59

(58) Field of Classification Search .............. 606/53–59
See application file for complete search history.

(56) References Cited

U.S. PATENT DOCUMENTS

| | | | |
|---|---|---|---|
| 4,444,181 A | 4/1984 | Wevers et al. | |
| 4,976,712 A * | 12/1990 | VanderSlik | 606/59 |
| 5,074,865 A | 12/1991 | Fahmy | |
| 5,207,676 A | 5/1993 | Canadell et al. | |
| 5,376,091 A | 12/1994 | Hotchkiss et al. | |
| 5,449,359 A | 9/1995 | Groiso | |
| 5,660,188 A | 8/1997 | Groiso | |
| 5,662,650 A | 9/1997 | Balley et al. | |
| 5,702,389 A | 12/1997 | Taylor et al. | |
| 5,728,095 A | 3/1998 | Taylor et al. | |
| 5,766,176 A | 6/1998 | Duncan | |
| 5,803,924 A | 9/1998 | Oni et al. | |
| 5,853,414 A | 12/1998 | Groiso | |
| 5,902,304 A | 5/1999 | Walker et al. | |
| 5,941,877 A | 8/1999 | Viegas et al. | |
| 5,944,719 A | 8/1999 | Leban | |
| 5,947,999 A | 9/1999 | Groiso | |
| 5,976,125 A | 11/1999 | Graham | |
| 5,984,925 A | 11/1999 | Apgar | |
| 5,993,476 A | 11/1999 | Groiso | |
| 6,080,153 A | 6/2000 | Mata et al. | |
| 6,093,188 A | 7/2000 | Murray | |
| 6,162,223 A | 12/2000 | Orsak et al. | |
| 6,162,224 A | 12/2000 | Huebner | |
| 6,171,308 B1 | 1/2001 | Bailey et al. | |
| 6,171,309 B1 | 1/2001 | Huebner | |
| 6,203,548 B1 | 3/2001 | Helland | |
| 6,235,029 B1 | 5/2001 | Faccioli et al. | |
| 6,293,949 B1 | 9/2001 | Justis et al. | |
| 6,340,361 B1 | 1/2002 | Kraus et al. | |
| 6,358,255 B1 | 3/2002 | Testa | |
| 6,364,881 B1 | 4/2002 | Apgar et al. | |
| 6,716,212 B1 | 4/2004 | Pickens | |
| 6,908,467 B2 | 6/2005 | Ip et al. | |

(Continued)

FOREIGN PATENT DOCUMENTS

WO WO/92/15258 9/1992

(Continued)

*Primary Examiner* — Alvin Stewart
*Assistant Examiner* — Stuart S Bray
(74) *Attorney, Agent, or Firm* — Charles E. Baxley

(57) ABSTRACT

An orthopedic apparatus is provided for bridging a first bone unit to a second bone unit. The apparatus is demonstrated on a finger joint, wherein one of the bones and/or ligaments and/or tendons of the joint is/are injured. A method for implanting and using the apparatus also is presented. The apparatus includes a reformably deformable span portion which is generally circular and preferably rhombic. By deforming or reforming the span portion, it can be repositioned laterally, and/or it can be rotated to allow range of rotary motion so as to promote healing.

12 Claims, 7 Drawing Sheets

U.S. PATENT DOCUMENTS

| | | |
|---|---|---|
| 2001/0049525 A1 | 12/2001 | Slocum |
| 2001/0051806 A1 | 12/2001 | Baillier |
| 2002/0004659 A1 | 1/2002 | Boudard et al. |
| 2002/0013584 A1 | 1/2002 | Termaten |
| 2002/0115998 A1* | 8/2002 | Schoenefeld ............ 606/59 |
| 2003/0009167 A1 | 1/2003 | Wozencroft |
| 2003/0191466 A1 | 10/2003 | Austin et al. |
| 2003/0225405 A1 | 12/2003 | Weiner |
| 2003/0225406 A1 | 12/2003 | Weiner et al. |
| 2003/0225407 A1 | 12/2003 | Estrada, Jr. |
| 2004/0044344 A1 | 3/2004 | Winquist et al. |
| 2004/0097944 A1 | 5/2004 | Koman et al. |
| 2004/0116925 A1 | 6/2004 | Gill et al. |
| 2004/0133199 A1 | 7/2004 | Coati et al. |
| 2004/0133200 A1 | 7/2004 | Ruch et al. |
| 2004/0138659 A1 | 7/2004 | Austin et al. |
| 2005/0015087 A1 | 1/2005 | Walulik et al. |
| 2005/0038425 A1 | 2/2005 | Werding et al. |
| 2005/0085810 A1 | 4/2005 | Lutz et al. |
| 2005/0085811 A1 | 4/2005 | Peckitt |
| 2005/0113829 A1 | 5/2005 | Walulik et al. |
| 2005/0149018 A1 | 7/2005 | Cooper et al. |
| 2005/0165394 A1 | 7/2005 | Boyce et al. |
| 2005/0171539 A1* | 8/2005 | Braun et al. ............ 606/61 |
| 2005/0203509 A1 | 9/2005 | Chinnaian et al. |
| 2005/0234452 A1 | 10/2005 | Malandain |
| 2005/0251135 A1 | 11/2005 | Riccione et al. |
| 2006/0015101 A1 | 1/2006 | Warburton et al. |
| 2006/0058796 A1 | 3/2006 | Hartdegen et al. |
| 2006/0184169 A1 | 8/2006 | Stevens |
| 2006/0217710 A1 | 9/2006 | Abdou |
| 2006/0235383 A1 | 10/2006 | Hollawell |
| 2006/0271043 A1 | 11/2006 | Gonzalez |
| 2007/0038217 A1 | 2/2007 | Brown et al. |
| 2007/0055233 A1 | 3/2007 | Brinker |
| 2007/0118116 A1 | 5/2007 | Feiler et al. |
| 2007/0123858 A1 | 5/2007 | Strub et al. |
| 2007/0161983 A1 | 7/2007 | Gresina et al. |
| 2007/0255280 A1 | 11/2007 | Austin et al. |
| 2007/0260243 A1 | 11/2007 | Kagami |
| 2008/0021451 A1 | 1/2008 | Coull et al. |
| 2008/0086123 A1 | 4/2008 | Gotfried |
| 2008/0091203 A1 | 4/2008 | Warburton et al. |
| 2008/0188852 A1 | 8/2008 | Matityahu |
| 2008/0195095 A1 | 8/2008 | Renard et al. |
| 2008/0221571 A1 | 9/2008 | Daluiski et al. |
| 2008/0221572 A1 | 9/2008 | Naegerl et al. |
| 2008/0221573 A1 | 9/2008 | Kumhyr |
| 2008/0255554 A1 | 10/2008 | Richter et al. |
| 2008/0269741 A1 | 10/2008 | Karidis |
| 2008/0281324 A1 | 11/2008 | Webb et al. |
| 2009/0018541 A1 | 1/2009 | Lavi |
| 2009/0024128 A1 | 1/2009 | Nakamura et al. |
| 2009/0036889 A1 | 2/2009 | Callender |
| 2009/0036891 A1 | 2/2009 | Brown et al. |
| 2009/0088751 A1 | 4/2009 | Mullaney |
| 2009/0099565 A1 | 4/2009 | Weiner et al. |
| 2009/0228006 A1 | 9/2009 | Mussolin |
| 2010/0036430 A1 | 2/2010 | Hartdegen et al. |
| 2010/0249779 A1 | 9/2010 | Hotchkiss |

FOREIGN PATENT DOCUMENTS

| | | |
|---|---|---|
| WO | WO/96/35385 | 11/1996 |
| WO | WO/99/02097 | 1/1999 |
| WO | WO/99/04714 | 2/1999 |
| WO | WO/2005/044117 | 5/2005 |
| WO | WO/2006/068682 | 6/2006 |
| WO | WO/2006/092863 | 9/2006 |
| WO | WO/2007/053887 | 5/2007 |
| WO | WO/2007/090543 | 8/2007 |
| WO | WO/2007/138659 | 12/2007 |
| WO | WO/2008/051064 | 5/2008 |
| WO | WO/2008/073238 | 6/2008 |

* cited by examiner

ORTHOPEDIC EXTERNAL FIXATOR AND METHOD OF USE

1. BACKGROUND OF THE INVENTION

A. Field of the Invention

The embodiments of the present invention relate primarily to orthopedic apparatuses, sometimes referred to as "fixators", which organize and/or control positioning at joints or fractures, and/or ranges of motion of juxtaposed bone units at joints. These apparatuses according to the embodiments of the present invention can be organized to impose or to relieve physical stresses associated with the bone units and/or with related ligaments and/or tendons. These apparatuses can be organized to all controlled rotation of the bones at the joint. In one embodiment of the present invention, when squeezed, the apparatus generally produces distraction, when relaxed the apparatus general produces contraction.

For clarity the embodiments of the present invention are set forth in context of a finger joint. It will, however, be apparent to orthopedic physicians and surgeons and to others that the embodiments of the present invention have comprehensive scope for application to many, many other joints and/or fractures, dislocations, tendon and/or ligament injuries and/or the like.

B. Description of the Prior Art

[1]Joint injuries often result in displacement of components of the joint and of bone fragments that have become fractured and dislocated in the injury.

[1]See, Fractures of the Proximal Interphalangeal Joints of the Fingers, C. Y. Ng, C. W. Oliver, Royal Infirmary of Edinburgh, Edinburgh, Scotland, J Bone Surgery [Br] 2009;91-B:705-12, ©2009 British Editorial Society if Bone and Joint Surgery doi: 10.1302/0301-620X.91B6. See, Treatment of Proximal Interphalangeal Dorsal Fracture-Dislocation Injuries with Dynamic External Fixation: a Pins and Rubber Band System, S. J. Ellis, R. Cheng, P. Prokopis, A Chetboun, S. W. Wolfe, E. A. Athanasian, A. J. Weiland, Journal of Hand Surgery, ©2007 American Society for Surgery of the Hand 0363-5023/07/32A08-0018$32.00/0, doi: 10.1016/j.jhsa.2007.07.001. Both references above are incorporated herein by reference thereto.

In the treatment of these injuries it is often required to create traction across a joint so that the components thereof are retained in appropriate relative dispositions during the healing process. It is also advantageous in certain cases to permit gentle controlled movement or relative rotation of the joint, which helps to mold the irregular surfaces and prevents eventual stiffness.

Numerous innovations for fixators have been provided in the prior art, which will here be described in chronological order to show advancement in the art, and which are incorporated herein by reference thereto. Even though these innovations may be suitable for the individual purposes to which they address, nevertheless, they differ from the present invention.

(1) U.S. Pat. No. 5,074,865 to Fahmy.

Referring now to the figures, in which like numerals indicate like parts, and particularly to FIG. 1, which is a diagrammatic side elevational view of the prior art distraction apparatus taught by U.S. Pat. No. 5,074,865 to Fahmy, U.S. Pat. No. 5,074,865 issued to Fahmy on Dec. 24, 1991 in U.S. class 606 and subclass 54 teaches a distraction apparatus 10 for maintaining a fractured joint 12 during healing, including a pair of pins 14 for insertion into bone 16 at positions proximal 18 to and distal 20 to the fractured joint 12, and a pair of stainless steel wire springs 22 that are adjustably attached to the pair of pins 14 to determine and resiliently maintain the relative spacing of pin insertions 24 into the bone 16 thus to retain the components of the fractured joint 12 during the healing process.

To provide initial distraction, unfortunately, Fahmy requires that the bones must first be manually separated before being held by the apparatus. "The insertion of the pins will take place under general or regional anaesthesia, and then while traction is applied to the finger the thicker of the two springs is attached to and between the pins, its position therealong being determined by location in the first or second grooves close to the finger."[Emphasis added].[2]

[2]Fahmy at col. 2, lines 20-25.

To alter the degree of distraction, unfortunately, Fahmy requires that the springs must be manually moved. "The degree of distraction can be initially fixed and subsequently altered easily by moving the two springs closer or spacing them further along the wires, or by adjusting the number of turns of one or both springs between the pins."[Emphasis added].[3]

[3]Fahmy at col. 2, lines 30-34.

Further, the springs of Fahmy are secured to the pins by a polymer/monomer. "The springs may be secured by adding a small amount of mixed past setting polymer and monomer where the springs are attached to the pins * * *."[Emphasis added].[4]

[4]Fahmy at col. 2, lines 38-40.

(2) International Patent Application Publication Number WO/1992/15258 to Bagits et al.

International Patent Application Publication Number WO/1992/15258 published to Bagits et al. on Sep. 17, 1992 in international patent classification A61B 17/60 teaches a disposable external fixator with apparatus for receiving pins known per se bored into the fractured bones for fixing them. The fixing apparatus includes a fixing rod with equidistantly spaced and aligned bores near its end parts, and provided with threaded parts at its ends. The diameters of the bores are larger than those of the pins received in them. The fixator further includes two stretching tubes slidably mounted onto the end parts of the fixing rod, and provided with bores of similar diameter, spacing, and position to those of the bores of the fixing rod. Finally, an internally threaded closing piece is shaped to facilitate the drawing and is screwed on the threaded parts formed at both ends of the fixing rod.

(3) U.S. Pat. No. 5,207,676 to Canadell et al.

U.S. Pat. No. 5,207,676 issued to Canadell et al. on May 4, 1993 in U.S. class 606 and subclass 54 teaches an external fixator for the correction and reduction of bone fragments, which includes a bar fastened to a biocompression system, on which bar and system are disposed the supports for fastening the pins inserted into the bones, the components of which supports are movable. A member permits the longitudinal displacement of a clip, while the biocompression system makes a reciprocating movement. A damping member cooperates with apparatus for regulating the force applied, which are disposed outside the bar. Graduated markings indicate the value of the force applied.

(4) U.S. Pat. No. 5,376,091 to Hotchkiss et al.

U.S. Pat. No. 5,376,091 issued to Hotchkiss et al. on Dec. 27, 1994 in U.S. class 606 and subclass 55 teaches a dynamic joint support having proximal and distal support sections, and apparatus for rigidly connecting each support section to bone, and a pair of hinges connecting each support section to each other and pivoting at the joint to cause movement of the support section and its corresponding attached bone through the movements of flexion and extension. The hinge may be driven in its movement by a gear mechanism that may be disengaged by way of a clutch. The dynamic joint support may also include a distraction mechanism for movement of the bones out of contact in the joint, while allowing for an active range of motion at the joint.

(5) International Patent Application Publication Number WO/1996/35385 to Bailey et al.

International Patent Application Publication Number WO/1996/35385 published to Bailey et al. on Nov. 14, 1996 in international patent classification A61B 17/56 teaches an external fixator for securing a first bone portion in a fixed relationship with respect to a second bone portion. The fixator includes a bone screw clamp for receiving a first bone screw that is connected to the first bone portion and which includes a spherical portion. The fixator further includes a bone screw clamp that is operable to receive a second bone screw that is connected to the second bone portion and which has a spherical portion. The fixator also includes a connection member having a radiographic window to permit radiographic examination of the bone fracture, as well as a cantilever member operable to secure the spherical portions of the first and second bone screw clamps to the connection member.

(6) International Patent Application Publication Number WO/1999/002097 to Helland.

International Patent Application Publication Number WO/1999/002097 published to Helland on Jan. 21, 1999 in international patent classification A61B 17/66 teaches a distraction apparatus for holding a fracture during the healing process. The apparatus includes screws or pins for insertion into a bone at points proximal and distal relative to a fracture site, and a pair of springs that can be connected externally between the screws or pins at spaced positions thereon. The springs act as an extension spring and a compression spring, respectively, between the screws or pins. The springs are connected at the spaced positions at distances relative to the bone that the springs will exert moments of force in order to obtain a desired torque load at the fracture site.

(7) International Patent Application Publication Number WO/1999/004714 to Nestorov.

International Patent Application Publication Number WO/1999/004714 published to Nestorov on Feb. 4, 1992 in international patent classification A61B 17/60 teaches an external fixator including threaded carriers with a through hole for receiving bone implants clamped by fixing nuts. The carriers are interconnected by compression-distraction mechanisms and/or ball and socket joints.

(8) U.S. Pat. No. 5,941,877 to Viegas et al.

U.S. Pat. No. 5,941,877 issued to Viegas et al. on Aug. 24, 1999 in U.S. class 606 and subclass 55 teaches a hand fracture, burn, and contraction treatment device that is capable of imparting a desired amount of long term force and moment to the interphalangeal and metacarpalphalangeal joints so as to effectively combat deformity due to burn scar or trauma, to prevent and/or correct contractures, and to reduce and immobilize fractures. The device includes two axial members slidably mounted within respective housings and joined by a spherical joint, with a slot to provide a selectable axis of increased range of motion. The device permits movement of one axial member with respect to the other axial member in up to five degrees of freedom. The device further provides for the adjustable mobilization of each axial member.

(9) U.S. Pat. No. 5,944,719 to Leban.

U.S. Pat. No. 5,944,719 issued to Leban on Aug. 31, 1999 in U.S. class 606 and subclass 59 teaches an external fixator for setting fractured bones, which includes a flexible, articulable column including a series of ball and socket members linked by a tensioning cable threaded therethrough. Tightening the cable forces the ball and socket members together and makes the column rigid. There is a mechanism for tightening the cable and keeping the cable in a tightened position to allow the bones to set without moving. A plurality of pivotable pin holders are arranged along the column for attaching to pins inserted into the fractured bones, thus attaching the column to the bones to be set. There is also a mechanism for fixing each pin holder into a rigid position so that there can be no pivoting motion after the proper position of the fixator has been achieved.

(10) U.S. Pat. No. 5,976,125 to Graham.

U.S. Pat. No. 5,976,125 issued to Graham on Nov. 2, 1999 in U.S. class 606 and subclass 32 teaches an external fixation apparatus for reduction and distraction of a joint injury, such as fracture or dislocation of the proximal and distal bones of a joint from a location external to the soft tissue of a patient. The device includes a proximal fixator, a distal fixator, a proximal wire inserted through the proximal fixator and into a proximal bone, a distal wire inserted through the distal fixator and into a distal bone, and an adjustable distraction mechanism connecting the proximal and distal fixators.

(11) U.S. Pat. No. 6,080,153 to Mata et al.

U.S. Pat. No. 6,080,153 issued to Mata et al. on Jun. 27, 2000 in U.S. class 606 and subclass 54 teaches an articulation element for the relative positioning of fixation bars or bone pins of an external fixator, which includes a plurality of pairs of jaws. The jaws have on their adjacent faces grooves that form a passage intended to receive a bar or a pin. A spring is interposed between the pairs of jaws. The grooves that form the passage are positioned and arranged so as to have an external opening allowing the bar or bone pin to be snapped in by pressure on it, from the opening of the jaw into the passage, and against the spring force that presses the adjacent faces of the jaws against one another. This force holds the articulation element on the bars or pins before locking of the articulation by way of a clamping shaft.

(12) U.S. Pat. No. 6,162,223 to Orsak et al.

U.S. Pat. No. 6,162,223 issued to Orsak et al. on Dec. 19, 2000 in U.S. class 606 and subclass 59 teaches a joint fixator apparatus that conforms to the natural axis of rotation of the joint in question, such as a patient's wrist or knee, to avoid the possibility of bone fragment displacement and/or fracture reduction. The apparatus includes two fixation rod sections or shaft sections with a spring module therebetween. The spring module is in the form of a flexible coupler that connects to respective ends of the external fixator rod. The module can include a removable clip to restrain the motion of the spring a desired amount, such as before healing takes place. The rods can be used to hold pin clamps that then hold bone pins for attachment to selected bones of the patient, such as above and below a joint or above and below a fracture. The pin clamps can be moved along the rod sections to provide distraction of the joints for a ligamentotaxis effect in reducing the fracture.

(13) U.S. Pat. No. 6,162,224 to Huebner.

U.S. Pat. No. 6,162,224 issued to Huebner on Dec. 19, 2000 in U.S. class 606 and subclass 59 teaches a bone fixator for repairing fractures of the distal radius and wrist. It includes, in the preferred embodiment, at least two generally parallel, spaced-apart elongate distal mounting pins with lower ends for mounting in the metacarpal bone and at least two generally parallel, spaced-apart elongate radial mounting pins with lower ends for mounting in the radius. A distal pin clamp assembly secures the distal pins to an elongate distal member. The clamp assembly and pins are movably coupled to the distal member for translational movement along its elongate axis and pivotal motion about a pivot axis generally perpendicular to the elongate axis of the distal member and the elongate axes of the distal pins. A pin mounting carriage holds the radial pins, and an elongate medial assembly is connected at one end to the pin mounting carriage for independent translational motion along an axis generally perpendicular to the elongate axes of the proximal mounting pins and the elongate axis of the medial assembly and coupled at the opposed end through a ball joint to the distal member.

(14) U.S. Pat. No. 6,171,309 to Huebner.

U.S. Pat. No. 6,171,309 issued to Huebner on Jan. 9, 2001 in U.S. class 606 and subclass 57 teaches a bone fixator for repairing fractures of the distal radius and wrist. It includes, in the preferred embodiment, at least two generally parallel spaced-apart elongate distal mounting pins with lower ends for mounting in the metacarpal bone and at least two generally parallel spaced-apart elongate radial mounting pins with lower ends for mounting in the radius. A distal pin clamp assembly secures the distal pins to an elongate distal member. The clamp assembly and pins are movably coupled to the distal member for translational movement along its elongate axis and pivotal motion about a pivot axis generally perpendicular to the elongate axis of the distal member and the elongate axes of the distal pins. The fixator further includes a proximal pin mounting block for securing the radial pins and an elongate medial assembly of adjustable length. The medial assembly is pivotally connected at one end to the pin mounting block for independent pivotal motion about an axis generally parallel to the elongate axes of the proximal mounting pins and coupled at the opposed end through a ball joint to the distal member.

(15) U.S. Pat. No. 6,203,548 B1 to Helland.

U.S. Pat. No. 6,203,548 B1 issued to Helland on Mar. 20, 2001 in U.S. class 606 and subclass 105 teaches a distraction apparatus for holding a fracture during the healing process. The apparatus includes screws or pins for insertion into a bone at points proximal and distal relative to a fracture site, and a pair of springs that can be connected externally between the screws or pins at spaced positions thereon. The springs act as an extension spring and a compression spring, respectively, between the screws or pins. The springs are connected at the spaced positions at distances relative to the bone that the springs will exert moments of force in order to obtain a desired torque load at the fracture site.

(16) U.S. Pat. No. 6,235,029 B1 to Faccioli et al.

U.S. Pat. No. 6,235,029 B1 issued to Faccioli et al. on May 22, 2001 in U.S. class 606 and subclass 54 teaches an orthopaedic device for the gradual correction of angular and longitudinal defects of elongated bones, which includes at least one first clamp for a first group of screws insertable in a proximal portion of a bone, at least one second clamp for a second group of screws insertable in a distal portion of the bone, and a longitudinal guide bar positioned externally of the limb to be corrected for slidably supporting the clamps. At least one of the clamps is selectively orientable about a substantially transverse axis for carrying out angular corrections of the bone. A compression/distraction device is movably coupleable with the clamps for carrying out longitudinal corrections of the bone. The orientably clamp is adjustable angularly in a predetermined geometric plane, as well as adjustable transversely for the group of bone screws carried by the clamp parallel to themselves for compensating for the lateral movement induced by the angular correction.

(17) United States Patent Application Publication Number US 2001/0049525 A1 to Slocum.

United States Patent Application Publication Number US 2001/0049525 A1 published to Slocum on Dec. 6, 2001 in U.S. class 606 and subclass 54 teaches a joint support attachable to a limb of an animal to limit movement of an associated limb joint substantially about a single axis. The joint support includes a radial element having a longitudinal axis and a transverse element having a longitudinal axis. The transverse element is pivotally connected to the radial element about an axis of rotation. The longitudinal axis of the radial element substantially intersects with the axis of rotation, and radial rotation of the radial element is restricted about the axis of rotation. The longitudinal axis of the transverse element is partially fixed relative to the radial element so that it is substantially coplanar with the longitudinal axis of the radial element and substantially offset from the axis of rotation.

(18) United States Patent Application Publication Number US 2001/0051806 A1 to Ballier.

United States Patent Application Publication Number US 2001/0051806 A1 published to Ballier on Dec. 13, 2001 in U.S. class 606 and subclass 54 teaches a fixation device with clamping jaws and with rods connecting the clamping jaws. The rods are adjustable axially and angularly for positioning relative to the clamping jaws and clampable in the desired position, and with fixation and retaining pins that are receivable in a clampable fashion in the clamping jaws. A fixation pin applicator can be connected in a releasable fashion to the clamping jaws. A fixation pin can be brought into a desired position by way of the fixation pin applicator.

(19) United States Patent Application Publication Number US 2002/0004659 A1 to Boudard et al.

United States Patent Application Publication Number US 2002/0004659 A1 published to Boudard et al. on Jan. 10, 2002 in U.S. class 606 and subclass 54 teaches a fixator including a rigid bar, two pin-holder assemblies that can be moved relative to this bar, and apparatus with which it is possible to immobilize each pin-holder assembly in a defined position relative to the bar. The bar has a cylindrical main part and a spherical part at one end. A first pin-holder assembly includes a one-piece body with a bore passing through it to permit its engagement by sliding on the cylindrical part of the bar. The second pin-holder assembly includes a one-piece body in which a recess is formed. This recess has a zone of partially spherical shape with a radius slightly greater than that of said spherical part. This zone can receive this spherical part with pivoting, without lateral play, and with a possibility of articulation of the second pin-holder assembly.

(20) U.S. Pat. No. 6,340,361 B1 to Kraus et al.

U.S. Pat. No. 6,340,361 B1 issued to Kraus et al. on Jan. 22, 2002 in U.S. class 606 and subclass 59 teaches an external fixator system that includes a clamp adapted to couple a fixator pin to a connecting rod. The clamp includes a slot for transversely receiving the connecting rod. A bolt is inserted through a bore passing transversely to the slot to engage a pin connector holding a fixator pin. The pin connector has a rod-engaging surface that wedges the connecting rod into the slot, thus increasing the clamp's rigidity by preventing rotation of the clamp around the rod and rotation of the pin connector in the clamp body. An aiming device attaches to at least two connecting rods to guide the insertion of fixator pins between the rods. The aiming device is adjustable to accommodate various distances between the rods and has different modes of attachment to the rods to enable the clamp installation either above or below the rods.

(21) United States Patent Application Publication Number US 2002/0013584 A1 to Termaten.

United States Patent Application Publication Number US 2002/0013584 A1 published to Termaten on Jan. 31, 2002 in U.S. class 606 and subclass 54 teaches a fixing device for orthopedic applications. At least one coupling member is mounted in the connecting rod of, or the guiding rod for, the clamping members, and intended for receiving orthopedic pins. The coupling member can be brought into a rigid or a flexible coupling position. Further, preferably, it has been provided for that in the flexible coupling position, the flexibility can be adjusted across a certain range.

(22) U.S. Pat. No. 6,358,255 B1 to Testa.

U.S. Pat. No. 6,358,255 B1 issued to Testa on Mar. 19, 2002 in U.S. class 606 and subclass 105 teaches a device especially for osteodistraction, configured for attachment to different bone parts that have been separated, and that are bound together by the device that holds the bones parts in a pre-set position and/or simultaneously exerts pressure for distancing or bringing together the bone parts. The device includes at least two elements configured for fastening to two bone parts that are separate from each other. The two elements are coupled together and movable along at least one pre-set direction, there being inserted between them an elastic element for providing a thrust in the distancing or traction direction. The device may be removably coupled to the bone parts to facilitate installation.

(23) United States Patent Application Publication Number US 2002/0115998 A1 to Schoenefeld.

United States Patent Application Publication Number US 2002/0115998 A1 published to Schoenefeld on Aug. 22, 2002 in U.S. class 606 and subclass 59 teaches an external fixator for securing a first bone portion in a fixed relationship with respect to a second bone portion, which includes a longitudinally extending rod and a bone screw clamping assembly. The bone screw clamping assembly receives at least one bone screw. The bone screw clamping assembly is mounted to the rod for relative universal movement about a point through which the rod passes, and is normally permitted to longitudinally translate along an axis defined by the rod.

(24) United States Patent Application Publication Number US 2003/0009167 A1 to Wozencroft.

United States Patent Application Publication Number US 2003/0009167 A1 published to Wozencroft on Jan. 9, 2003 in U.S. class 606 and subclass 55 teaches a device that immobilizes bones of a patient, such as a surgically exposed femur and tibia, during a knee replacement operation. The device has a vertical frame including a pair of first members and at least one second member bracing the first members. A support mechanism is mounted on the first members to permit adjustment of the height of the support mechanism. A first and second series of cantilever members are supported by the support mechanism. First and second bone engagement mechanisms are mounted on respective cantilever members and engage a patient's surgically exposed first and second bones.

(25) United States Patent Application Publication Number US 2003/0191466 A1 to Austin et al.

United States Patent Application Publication Number US 2003/0191466 A1 published to Austin et al. on Oct. 9, 2003 in U.S. class 606 and subclass 54 teaches devices and methods for aligning fragments of a fractured bone or for positioning bones. In some embodiments, fixation devices and anatomical features are modeled with the aid of a computer, and the model is used to determine how an actual fixation device should be configured to align or position the bones.

(26) United States Patent Application Publication Number US 2003/0225405 A1 to Weiner.

United States Patent Application Publication Number US 2003/0225405 A1 published to Weiner on Dec. 4, 2003 in U.S. class 606 and subclass 54 teaches an external fixator that includes a main body and an outrigger for extending over a fractured joint, such as a wrist joint. The main body can be positioned next to a right arm or flipped over and positioned next to a left arm. The outrigger is attachable to extend either to the left or to the right of the main body, as appropriate. A distal body is removably connectable to the distal end of the main body, and the distal body can be affixed to bone on the opposite side of the fracture to immobilize the joint where the fracture occurs. The distal body is connected to the main body with an adjustable securement section that provides six degrees of adjustment freedom. The outrigger is attached to the main body through a slide plate in a dual rail configuration that provides two dimensions of adjustment. Fragment pin supports ride in a track of the outrigger and provide seven degrees of adjustment freedom for directed fixation of fragments at the fracture site. The major components of the fixator are molded of plastic. A surgical technique using the fixator includes immobilizing the joint for an initial healing duration and retaining fragment pins in place during a secondary healing duration.

(27) United States Patent Application Publication Number US 2003/0225406 A1 to Weiner et al.

United States Patent Application Publication Number US 2003/0225406 A1 published to Weiner et al. on Dec. 4, 2003 in U.S. class 606 and subclass 54 teaches an external fixator that includes a main body and an outrigger for extending over a fractured joint, such as a wrist joint. The main body can be positioned next to a right arm or flipped over and positioned next to a left arm. The outrigger is attachable to extend either to the left or to the right of the main body, as appropriate. A distal body is removably connectable to the distal end of the main body, and the distal body can be affixed to bone on the opposite side of the fracture to immobilize the joint where the fracture occurs. The distal body is connected to the main body with an adjustable securement section that provides six degrees of adjustment freedom. The outrigger is attached to the main body through a slide plate in a dual rail configuration that provides two dimensions of adjustment. Fragment pin supports ride in a track of the outrigger and provide seven degrees of adjustment freedom for directed fixation of fragments at the fracture site. The outrigger is pivotally adjustable relative to the main body and includes track portions separated by a wrap around angle. The major components of the fixator are molded of plastic. A surgical technique using the fixator includes immobilizing the joint for an initial healing duration and retaining fragment pins in place during a secondary healing duration.

(28) United States Patent Application Publication Number US 2003/0225407 A1 to Estrada, Jr.

United States Patent Application Publication Number US 2003/0225407 A1 published to Estrada, Jr. on Dec. 4, 2003 in U.S. class 606 and subclass 54 teaches a fixator that is an apparatus for repairing fractures of the distal radius and wrist. Distal, pivot, distraction, and radial members provide an anatomically contoured, radiolucent apparatus that permits the wrist to move through a substantially normal range of motion. Apparatus for distraction of the bones by the fixator is also provided. The fixator may be affixed to the lower arm and hand by spaced-apart elongate distal mounting pins with lower ends adapted or mounting in the metacarpal bone and by spaced-apart elongate radial mounting pins with lower ends adapted for mounting in the radius.

(29) United States Patent Application Publication Number US 2004/0044344 A1 to Winquist et al.

United States Patent Application Publication Number US 2004/0044344 A1 published to Winquist et al on Mar. 4, 2004 in U.S. class 606 and subclass 54 teaches an external fixation or adjustable frame structure. A frame structure is retained in any assembled configuration in order to allow final adjustments to be made prior to the final securement of the frame assembly in the precisely desired configuration by closure of each clamp member. In this way, an entire frame assembly is capable of being constructed, adjusted, and readjusted in order to assure each component is oriented in the precisely desired position prior to final closure of the clamping members. In one preferred embodiment, the clamping members employed in the frame structure incorporate friction pins internally mounted in each clamp, and which engage the rod member once this rod is inserted into the jaws of the clamp. In this way, any rod member inserted into the clamping jaws contacts the surface of the jaws and the friction pin preventing the rod member from sliding or moving relative to the clamp. In addition, by incorporating a uniquely constructed, moving wedge plate that is adjustably engageable with any cooperating anchor pin, secure affixation of the mounting member with the anchor pins of any diameter is achieved regardless of the orientation configuration or diameter of the anchor pin.

(30) U.S. Pat. No. 6,716,212 B1 to Pickens.

U.S. Pat. No. 6,716,212 B1 issued to Pickens on Apr. 6, 2004 in U.S. class 606 and subclass 54 teaches a universal modular external fixation system for immobilizing bone fragments in long bone fractures. The universal modular external fixation system includes a frame assembly including a plurality of pins to be coupled to various portions of a fractured bone. The external sections of the pins are fixated to a variety of different coupling devices to attach to a series of connecting bars along the length of the fractured bone. A plurality of connecting members interconnect the connecting bars, thereby securing the pins, and thus the bone sections, to aid in proper healing of the fracture(s).

(31) United States Patent Application Publication Number US 2004/0097944 A1 to Koman et al.

United States Patent Application Publication Number US 2004/0097944 A1 published to Koman et al. on May 20, 2004 in U.S. class 606 and subclass 72 teaches a fixation device for treatment of orthopedic indications. The device, preferably, includes a first portion and a second portion that may be incrementally and independently articulated relative to each other to promote healing of an orthopedic indication. One or more worm gear assemblies may be used to incrementally adjust articulation of the first portion and the second portion relative to each other.

(32) United States Patent Application Publication Number US 2004/0116925 A1 to Gill et al.

United States Patent Application Publication Number US 2004/0116925 A1 published to Gill et al. on Jun. 17, 2004 in U.S. class 606 and subclass 54 teaches a frame for attaching to a patient, a stereoguide, and a member for attaching to a patient. A method for manufacturing the frame, member, and stereoguide is also provided. The frame, member, and stereoguide are constructed from a composite material including a matrix material and electromagnetically inert fibres.

(33) United States Patent Application Publication Number US 2004/0133199 A1 to Coati et al.

United States Patent Application Publication Number US 2004/0133199 A1 published to Coati et al. on Jul. 8, 2004 in U.S. class 606 and subclass 54 teaches an external fixation device having a carrying structure of interconnected elements, which includes an extendible central body, and clamps for bone screws, respectively, articulated on opposed ends of the central body. The central body includes two parts telescoping slidable one on the other. Each of the parts include a first portion of elongate shape formed integrally with a second end portion of substantially cylindrical shape. The first portions of the parts are slidably coupled to each other by way of a driving groove formed longitudinally in one first portion and a corresponding slide formed longitudinally in the other first portion, and apparatus is provided in the parts for stopping their sliding movement, which is characterized in that it further includes at least one plate having a predetermined contour shape and thickness, at least one recess formed on the surface of at least one of the interconnected elements and having its contour shape matching the contour shape of the at least one plate, and apparatus for releasably securing the at least one plate in the at least one recess.

(34) United States Patent Application Publication Number US 2004/0133200 A1 to Ruch et al.

United States Patent Application Publication Number US 2004/0133200 A1 published to Ruch et al on Jul. 8, 2004 in U.S. class 606 and subclass 54 teaches an apparatus to reduce bony fragments and maintain a human's wrist or hand in a healing position. The apparatus may include a first clamp assembly operable to removably mount to an external fixator when the external fixator is coupled to a first bone of a human. A second clamp assembly may be releasably engaged with at least one bone pin embedded in a second bone of a human. A connector rod may be provided to join the first clamp assembly to the second clamp assembly.

(35) United States Patent Application Publication Number US 2004/0138659 A1 to Austin et al.

United States Patent Application Publication Number US 2004/0138659 A1 published to Austin et al. on Jul. 15, 2004 in U.S. class 606 and subclass 54 teaches apparatuses and methods for externally fixing and precisely adjusting fractures, such as fractures near the ankle. In one embodiment, an external fixation apparatus includes a first member attachable to a first bone segment through pins and a second member coupled to the first member through a lockable ball joint. First and second ends of the second member may be translated transversely relative to a longitudinal axis of the second member, and a pin clamp is coupled to and rotatable about the second member through a lockable joint and attachable to a second bone segment. The pin clamp and the second member may be releasably coupled.

(36) United States Patent Application Publication Number US 2005/0015087 A1 to Walulik et al.

United States Patent Application Publication Number US 2005/0015087 A1 published to Walulik et al on Jan. 20, 2005 in U.S. class 606 and subclass 54 teaches a frame assembly for an external fixation device and associated method. The frame assembly includes a first arc segment and a second arc segment. The first arc segment is for interconnection to a first bone portion. The second arc segment is for interconnection to a second bone portion. The first arc segment is coupled to the second arc segment for controlled relative rotation.

(37) United States Patent Application Publication Number US 2005/0038425 A1 to Werding et al.

United States Patent Application Publication Number US 2005/0038425 A1 published to Werding et al. on Feb. 17, 2005 in U.S. class 606 and subclass 54 teaches a device for externally immobilizing broken bones, particularly, bones of the extremities. Interspaced bone pins provided for insertion into the bone while passing through the skin and soft-tissue mantle are arranged on a multi-articulation rod. This multi-articulation rod can be placed on the outside of the body while extending along a broken bone, and includes elements that are interconnected in a ball-and-socket type manner, which can be fixed in selected relative positions. The elements have a ball on one end and a ball socket on the other end. The ball of one element is located inside the ball socket of an adjacent element. The ball and ball socket each geometrically extend over more than one hemisphere, and the surfaces of the ball and ball socket are roughened.

(38) United States Patent Application Publication Number US 2005/0085810 A1 to Lutz et al.

United States Patent Application Publication Number US 2005/0085810 A1 published to Lutz et al. on Apr. 21, 2005 on U.S. class 606 and subclass 54 teaches an external fixation system having clamps, rods, and pins having anti-magnetic core parts and a non-conductive sheath part covering essentially the exterior surfaces of the core part. The rods, pins, and clamps are especially MRI safe for a patient when used in any frame configuration for fractures of the upper and lower extremities and pelvis. The usual MRI field parameters of a static field of 2 Tesla, a time-varying filed of max. 20 Tesla/sec, and a specific absorption rate (SAR) of max. 0.4 Watts/kg averaged over the whole body of the patient apply.

(39) United States Patent Application Publication Number US 2005/0085811 A1 to Peckitt.

United States Patent Application Publication Number US 2005/0085811 A1 published to Peckitt on Apr. 21, 2005 in U.S. class 606 and subclass 55 teaches a spiral distraction device including anchoring apparatus for attachment of the device to each side of a patient's existing mandible. A conjoined intermediate bar attaches to and transports moveable bone pieces on each side of the patient's mandible towards each other in a spiral vector that is larger than the patient's anatomical mandible contour.

(40) International Patent Application Publication Number WO/2005/044117 to Biedermann et al.

International Patent Application Publication Number WO/2005/044117 published to Biedermann et al. on May 19, 2005 in international patent class A61B 17/70 teaches an elastic element that is used in a stabilizing device for bones or vertebrae. The elastic element is embodied as a substantially cylindrical member having a first end and an opposite second end. At least one of the opposite ends of the cylindrical member is provided with a coaxial bore that includes a female thread that is connected to a shaft and/or a head of a bone screw or rod section.

(41) United States Patent Application Publication Number US 2005/0113829 A1 to Walulik et al.

United States Patent Application Publication Number US 2005/0113829 A1 published to Walulik et al. on May 26, 2005 in U.S. class 606 and subclass 54 teaches an external fixation device that includes a frame assembly having a first arc segment and a second arc segment. The first arc segment is for interconnection to a first bone portion. The second arc segment is for interconnection to a second bone portion. The first arc segment is coupled to the second arc segment for relative rotation. The external fixation assembly additionally includes an articulating module. The articulating module includes a central member, a first pivot segment, and a second pivot segment. The first pivot segment is coupled to the central member for driven rotation about a first pivot axis. The second pivot segment is coupled to the central member for driven rotation about a second pivot axis. The second pivot axis is substantially perpendicular to the first pivot axis.

(42) U.S. Pat. No. 6,908,467 B2 to Ip et al.

U.S. Pat. No. 6,908,467 B2 issued to Ip et al. on Jun. 21, 2005 in U.S. class 606 and subclass 72 teaches a fixation device for internally or externally fixing fractures, which includes at least one nitinol wire having an S-shaped section and two ends. Each of the two ends forms a hook for hooking into a bone section of a fractured bone. This device can be made from nitinol that has a transformation temperature between 25° C. and 35° C. In addition, this device can have a diameter between 0.6 mm and 5 mm. The device can be inserted using the following process that starts by cooling the wire below a transfer temperature so that the nitinol wire forms in a martensite state. Next, the nitinol wire is inserted into a interphalangeal bone underneath a patients skin. Next, the nitinol wire heats up inside a patients body above the transfer temperature. Finally, the wire transforms from a martensite state to an austenite state wherein the nitinol wire elongates in a longitudinal direction to generate a distraction force.

(43) United States Patent Application Publication Number US 2005/0149018 A1 to Cooper et al.

United States Patent Application Publication Number US 2005/0149018 A1 published to Cooper et al. on Jul. 7, 2005 in U.S. class 606 and subclass 54 teaches an external foot/ankle fixation device having a one-piece frame component and a positionable cross bar that allows the attachment of generally anterior/posterior directed fixation wires or rods emanating from the foot/ankle of a patient. The external fixation device provides a stable fixation platform, both in-plane and out-of-plane of the object of fixation, e.g. foot or ankle. The fixation device through the cross bar also provides various degrees of angulation of anterior/posterior directed wires in two planes. Posterior angulation components may be provided to the posterior portion of the frame component, which provide additional fixation wire/rod angulation variations. Compression rails may also be provided. An optional elevator component may be attached to the bottom of the frame component, which does not obstruct access to the soft tissues on the bottom of the foot. The elevator component protects the bottom of the foot from contaminated surfaces.

(44) United States Patent Application Publication Number US 2005/0165394 A1 to Boyce et al.

United States Patent Application Publication Number US 2005/0165394 A1 published to Boyce et al. on Jul. 28, 2005 in U.S. class 606 and subclass 54 teaches a method of and system for attaching an orthopedic member to bone. The orthopedic member is positioned with respect to a bone segment. A plurality of pins are then driven through the orthopedic member and into the bone segment to secure the orthopedic member to the bone segment.

(45) United States Patent Application Publication Number US 2005/0203509 A1 to Chinnaian et al.

United States Patent Application Publication Number US 2005/0203509 A1 published to Chinnaian et al. on Sep. 15, 2005 in U.S. class 606 and subclass 54 teaches a fixation device employed to affix two or more segments of bone in a desired spatial relationship. Embodiments of the fixation device secure and maintain a bone fracture or fractures in proper alignment during the healing process, as well as permit slight movement or micro-motion therebetween to promote healing. In some applications, embodiments of the fixation device place the bone segments under continuous and adjustable compression or distraction, while still allowing slight movement or micro-motion at the bone segment interface.

(46) United States Patent Application Publication Number US 2005/0234452 A1 to Malandain.

United States Patent Application Publication Number US 2005/0234452 A1 published to Malandain on Oct. 20, 2005 in U.S. class 606 and subclass 61 teaches an implantable medical device and methods of use thereof for supporting a structure. The structure supported can include a bony structure. The device includes a support element having a top portion, and a bottom portion having a bottom surface and one or more apertures passing therethrough. The bottom surface of the support element includes a receiver configured to receive a plurality of anchor assemblies. Each of the anchor assemblies includes apparatus for locking the anchor assembly to the support element, and a base having a head and apparatus for locking the base to the anchor assembly. When assembled, the head of the base for the anchor assembly may not pass through the support element.

(47) United States Patent Application Publication Number US 2005/0251135 A1 to Riccione et al.

United States Patent Application Publication Number US 2005/0251135 A1 published to Riccione et al. on Nov. 10, 2005 in U.S. class 606 and subclass 54 teaches an external fixation assembly for bone fusion. The assembly includes an extension arm having a fixation joint portion and a pin element moveably disposed along the extension arm defining a first joint portion. The assembly further includes a plurality of connecting pins for bone fusion. Each of the connecting pins is configured to engage with bone matter for bone fusion and to singly attach to one of the joint portions for support.

(48) United States Patent Application Publication Number US 2006/0015101 A1 to Warburton et al.

United States Patent Application Publication Number US 2006/0015101 A1 published to Warburton et al. on Jan. 19, 2006 in U.S. class 606 and subclass 62 teaches an intramedullary fixation assembly usable with different long bone types and a guide assembly for guiding deployment of the intramedullary fixation assembly. The intramedullary fixation assembly includes a fixation member that has ends and a curved body extending between the ends. The curved body of the fixation member has a radius of curvature configured to extend through the medullary canal regardless of the long bone anatomy. Fasteners fix the fixation member to the bone fragments and are guided by a guide assembly. The guide assembly includes a guide body defining openings configured to guide the fasteners through openings defined in the fixation member and into the bone fragments. A fixation end of the guide body includes a pair of opposing, converging surfaces that are configured to engage in a positive fit, with an exposed end of the fixation member accessible through the side aperture in the first fragment.

(49) International Patent Application Publication Number WO/2006/068682 to Greenhalgh et al.

International Patent Application Publication Number WO/2006/068682 published to Greenhalgh et al. on Jun. 29, 2006 in international patent class A61B 17/60 teaches an expandable support device and methods of using the expandable support device. The expandable support device can be rotatably and inflatably deployed by a deployment tool. The deployment tool can engage a notch on the expandable support device and deliver a torque to the expandable support device. The deployment tool can inflate and expand the expandable support device.

(50) United States Patent Application Publication Number US 2006/0184169 A1 to Stevens.

United States Patent Application Publication Number US 2006/0184169 A1 published to Stevens on Aug. 17, 2006 in U.S. class 606 and subclass 54 teaches a system for stabilizing bone. The system includes a fixing block, a pin having a far end that is adapted to be fixed directly into bone and a near end that enters the fixing block, and a frame on which the fixing block is fixable. The pin enters the fixing block in a non-orthogonal manner in order to permit the pin to enter the bone with an orientation that is non-orthogonal to the bone's surface, thereby permitting the pin to engage more of the bone.

(51) International Patent Application Publication Number WO/2006/092863 to Nakamura et al.

International Patent Application Publication Number WO/2006/092863 published to Nakamura et al. on Sep. 8, 2006 in international patent class A61B 17/60 teaches an external wound fixing device that allows a bone and a bone piece to be moved freely and deformation thereof to be corrected. The external wound fixing device includes a pair of holding members for holding/securing rod-like members that are inserted, respectively, into a first part and a second part of a bone on opposite sides of a virtual fulcrum, and a coupling member for coupling the holding members. The virtual fulcrum is determined by any one of the center of deformation, the center of rotation of bone pieces holding a fracture part or a correction bone cut part between them, and the movable center of a joint part. The coupling member has a pair of arms fixed rotatably to one end of each of the holding members, respectively, and the pair of arms are coupled rotatably. Rotational axes of these arms are directed toward the virtual fulcrum.

(52) United States Patent Application Publication Number US 2006/0217710 A1 to Abdou.

United States Patent Application Publication Number US 2006/0217710 A1 published to Abdou on Sep. 28, 2006 in U.S. class 606 and subclass 54 teaches skull fixation assemblies and corresponding components. The assemblies include a multi-axial occipito-cervical connection system that enables elongate interconnectors, such as rods, to be coupled in a manner that permits relative movement in one or more planes. The system includes a locking mechanism that can be actuated to lock the relative positions of the elongate interconnector.

(53) United States Patent Application Publication Number US 2006/0235383 A1 to Hollawell.

United States Patent Application Publication Number US 2006/0235383 A1 published to Hollawell on Oct. 19, 2006 in U.S. class 606 and subclass 54 teaches a fixator for use in the reconstruction of acute, chronic, and traumatic injuries to the upper and lower extremities. The fixator has a clamping system that allows for the snapping in of pins and rails, and for multi-planar fixation of bones.

(54) United States Patent Application Publication Number US 2006/0271043 A1 to Gonzalez.

United States Patent Application Publication Number US 2006/0271043 A1 published to Gonzalez on Nov. 30, 2006 in U.S. class 606 and subclass 55 teaches a user-attached, manually operated, fluid-driven arm lift device for people who have difficulties in lifting an arm unassisted, which includes a base support member adapted to fit about a portion of a side rib area of a human, a base support member attachment mechanism connected to the base support member and adapted to removably attach the base support member to the human, an arm support member having a top end and having a bottom end and being hingedly connected to the base support member at its top end, a fluid-driven piston cylinder and drive rod system connected to the base support member at the system bottom end and to the arm support member at system top end, a manually operated fluid pump and a fluid reservoir, and a fluid release mechanism.

(55) United States Patent Application Publication Number US 2007/0038217 A1 to Brown et al.

United States Patent Application Publication Number US 2007/0038217 A1 published to Brown et al. on Feb. 15, 2007 in U.S. class 606 and subclass 57 teaches an orthopaedic fixation clamp for use in an external fixation system and its method of use.

(56) United States Patent Application Publication Number US 2007/0055233 A1 to Brinker.

United States Patent Application Publication Number US 2007/0055233 A1 published to Brinker on Mar. 8, 2007 in U.S. class 606 and subclass 54 teaches a system for externally repairing fractured bones and facilitating alignment of displaced fractured bone segments without requiring use of an external ring fixator system and tension wires. The system includes at least one panel member having a plurality of apertures extending from a first side to a second side of the panel member. At least two pin carriers are capable of being inserted into at least two of the plurality of apertures in the at least one panel member. The pin carriers, upon insertion into one of the plurality of apertures in the panel member, are longitudinally fixed relative to the aperture, but capable of rotation within the aperture. At least two half-pins are capable of insertion into a pin carrier, following insertion of the one pin carrier into one of the plurality of apertures provided in the panel member, toward subsequent securement to a fractured bone segment. Rotation of a pin carrier causes an associated half-pin inserted therein to move longitudinally with respect to the panel member to, in turn, reposition the fractured bone segment affixed to the half-pin, relative to the panel member.

(57) International Patent Application Publication Number WO/2007/053887 to Allison.

International Patent Application Publication Number WO/2007/053887 published to Allison on May 18, 2007 in international patent class A61B 17/60 teaches an external fixator for assisting healing of a fracture in a bone, which comprises a securing portion that defines a void, and an elongate bracket portion extends from the securing portion. The bracket portion is arranged to engage one or more first percutaneous bone fasteners locatable in the bone on a first side of the fracture. In use, one or more second percutaneous fasteners are located in the bone on a second side of the fracture so that the second fasteners extend into the void of the securing portion. The void can be filled with a cement compound to secure the second bone fasteners in place with respect to the securing portion.

(58) United States Patent Application Publication Number US 2007/0118116 A1 to Feiler et al.

United States Patent Application Publication Number 2007/0118116 A1 published to Feiler et al. on May 24, 2007 in U.S. class 606 and subclass 54 teaches a surgical appliance for assisting in the repair of a fractured bone, such as a scaphoid bone. The device includes first and second adjustably interconnected and spaced apart limb clamping jaws that are transparent to x-ray radiation and are relatively movable toward and away from one another, and a rotatable disk carried by the first jaw. The disk has a plurality of bores angularly disposed therein for selectively aligning a guide wire to be drilled percutaneously into the fractured bone. Each of the bores are in communication with the space between the first and second jaws, and the longitudinal axes of the bores are directed to a common point intermediate the first and second jaws.

(59) United States Patent Application Publication Number US 2007/0123858 A1 to Strub et al.

United States Patent Application Publication Number 2007/0123858 A1 published to Strub et al. on May 31, 2007 in U.S. class 606 and subclass 54 teaches an external fixation device having a frame including at least one rod that takes up mechanical loads. The frame and bone are connected via connecting apparatus, known per se, in particular bone-retaining pins. This connecting apparatus in turn is connected to the frame via clamping jaws. These clamping jaws permit detachable fixing and arbitrary arrangement and grouping on the frame. A module can be mounted on the frame. By way of the module, a movement of two bone fragments relative to one another can be effected. It has at least two components. The first of the at least two components can be connected to the frame. The second of the at least two components can be connected to at least one clamping jaw of a connecting apparatus that is connected to a bone fragment.

(60) United States Patent Application Publication Number US 2007/0161983 A1 to Cresina et al.

United States Patent Application Publication Number US 2007/0161983 A1 published to Cresina et al. on Jul. 12, 2007 in U.S. class 606 and subclass 54 teaches an external fixation system for a bone and associated method. The fixation system includes a proximal frame defining a continuous proximal boundary, a distal frame defining a continuous distal boundary, and at least one frame connector configured for interconnecting the proximal and distal frames at any position along at least one of the proximal and distal boundaries.

(61) International Patent Application Publication Number WO/2007/090543 to Wolter et al.

International Patent Application Publication Number WO/2007/090543 published to Wolter et al. on Aug. 16, 2007 in international patent class A61B 17/60 teaches a fixation system for bone, which includes a connecting support, at least one bone screw that can be inserted into a through bore of the connecting support, and a sensor and telemetry system. The sensor and telemetry system is arranged on a separate plate that can be joined to the connecting support.

(62) United States Patent Application Publication Number US 2007/0255280 A1 to Austin et al.

United States Patent Application Publication Number US 2007/0255280 A1 published to Austin et al. on Nov. 1, 2007 in U.S. class 606 and subclass 54 teaches apparatuses and methods for externally fixing and precisely adjusting fractures, such as fractures near the ankle. In one embodiment, an external fixation apparatus includes a first member attachable to a first bone segment through pins, and a second member coupled to the first member through a lockable ball joint. First and second ends of the second member may be translated transversely relative to a longitudinal axis of the second member. A pin clamp is coupled to and rotatable about the second member through a lockable joint and attachable to a second bone segment. The pin clamp and the second member may be releasably coupled.

(63) United States Patent Application Publication Number US 2007/0260243 A1 to Kagami.

United States Patent Application Publication Number US 2007/0260243 A1 published to Kagami on Nov. 8, 2007 in U.S. class 606 and subclass 57 teaches a tower-shaped frame provided to stand upright on a positionable platform, and a bone correction rod held by an elevating supporter. The elevating supporter is mounted on the tower-shaped frame to be adjustably movable up and down. A bone correction rod and a weight receiver are suspended from the elevating supporter to be movable up and down so as to apply a load of weights to the bone correction element as a bone correction force. When the bone correction device is used, a height of the elevating supporter is adjusted depending on a size, a posture of a body of a patient, and a position of the patient, and so forth, and a necessary weight is placed on the weight receiver depending on the symptom of the patient, and so forth. When the bone correction element is applied to an affected part, a pressing force is applied to the affected part in proportion to the weights, and hence if the pressing force is continuously applied to the affected part, an obstinate strain of a physique can be corrected.

(64) International Patent Application Publication Number WO/2007/138659 to Hirata et al.

International Patent Application Publication Number WO/2007/138659 published to Hirata et al. on Dec. 6, 2007 in international patent class A61B 17/60 teaches an external fixator for imparting extremely high degrees of freedom to insertion directions of pins. The fixator is provided with a plural number of pins to be inserted into a bone, ball joints to be, respectively, connected to these pins, and a rod-shaped member having a plural number of connectors for connecting the ball joints together. The rod-shaped member enables the adjustment of the positions of the connectors at least in the longitudinal direction of the rod-shaped member.

(65) United States Patent Application Publication Number US 2008/0021451 A1 to Coull et al.

United States Patent Application Publication Number US 2008/0021451 A1 published to Coull et al. on Jan. 24, 2008 in U.S. class 606 and subclass 54 teaches an external fixator for treating a fracture of a long bone, which has six extension arms that are extendable out of and retractable into a main body. The six extension arms are arranged into two sets of three, with each set of three extension arms being able to support a fixation ring. Each extension arm is pivotable at a joint and extendable so as to allow the ring to be set at a wide range of angular positions relative to the main body. The three extension arms and the ring each define a wrap angle about the axis of the long bone being treated. The longitudinal position of each extension arm can be changed either with a coarse adjustment capability or with a fine adjustment capability, with the coarse adjustment capability being through rotation of a thumb wheel. The six extension arms are also arranged into three opposing pairs, with each pair of extension arm shafts being disposed in an abutting relationship in the main body so that the extension arm shafts extend or retract out opposing sides of the main body.

(66) United States Patent Application Publication Number US 2008/0086123 A1 to Gotfried.

United States Patent Application Publication Number US 2008/0086123 A1 published to Gotfried on Apr. 10, 2008 in U.S. class 606 and subclass 59 teaches apparatus and method for treating a bone of a body of a patient, which includes a first member, at least a portion of which is radiolucent and arranged to be attached to the bone, an attachment member for attaching the first member to the bone, and a second member, at least a portion of which is radiolucent and arranged at least partly outside of the body of the patient and coupled to the first member. The second member guides the attachment member to facilitate attachment of the first member to the bone via the attachment member. The partially radiolucent composition of the first and second members facilitates attachment of the first member to the bone while imaging the apparatus, i.e., subjecting the apparatus and bone to X-ray imaging.

(67) United States Patent Application Publication Number US 2008/0091203 A1 to Warburton et al.

United States Patent Application Publication Number US 2008/0091203 A1 published to Warburton et al. on Apr. 17, 2008 in U.S. class 606 and subclass 62 teaches an intramedullary fixation assembly usable with different long bone types, and a guide assembly for guiding deployment of the intramedullary fixation assembly. The intramedullary fixation assembly includes a fixation member that has ends and a curved body extending between the ends. The curved body of the fixation member has a radius of curvature configured to extend through the medullary canal, regardless of the long bone anatomy. Fasteners fix the fixation member to the bone fragments and are guided by a guide assembly. The guide assembly includes a guide body defining openings configured to guide the fasteners through openings defined in the fixation member and into the bone fragments. A fixation end of the guide body includes a pair of opposing, converging surfaces that are configured to engage in a positive fit, with an exposed end of the fixation member accessible through the side aperture in the first fragment.

(68) International Patent Application Publication Number WO/2008/051064 to Anguiano.

International Patent Application Publication Number WO/2008/051064 published to Anguiano on May 2, 2008 in international patent classification A61B 17/60 teaches an all-metal device made from preformed elements welded to two basic sections that provide a lengthening or retraction effect as required, and which once assembled, operate telescopically. The device is for use in plastic, reconstructive, and trauma surgery on the hand or the metacarpal and metatarsal phalanges. The device can be locked using a variety of readily-available elements.

(69) International Patent Application Publication Number WO/2008/073238 to Cresina et al.

International Patent Application Publication Number WO/2008/073238 published to Cresina et al. on Jun. 19, 2008 in international patent classification A61B 17/64 teaches an external fixation system for a joint having a first and second bone and defining an anatomical axis of rotation. The fixation system can include a proximal frame couplable to the first bone and a distal frame couplable to the second bone. A first connector can include a first member pivotally coupled to a second member at a first pivot axis. A second connector can include a third member pivotally coupled to a fourth member at a second pivot axis. The first and second connectors are mountable between the proximal and distal frames at a location so that the first and second pivot axes are coaxial with the anatomical axis of rotation.

(70) United States Patent Application Publication Number US 2008/0188852 A1 to Matityahu.

United States Patent Application Publication Number US 2008/0188852 A1 published to Matityahu on Aug. 7, 2008 in U.S. class 606 and subclass 54 teaches a medical apparatus and a method of use for use with an outrigger and at least one fastening pin to reposition first and second portions of a bone of a mammalian body. The apparatus includes a framework and a first fastening assembly for coupling the framework to the outrigger, and thus the at least one fastening pin and the first end portion of the bone. The first end portion of an elongate pin is provided with a sharpened tip for penetrating the second portion of the bone. A second fastening assembly couples the second end portion of the elongate pin to the framework. At least one adjustment assembly is carried by at least one of the framework and the first and second fastening assemblies for moving the first end portion of the elongate pin relative to the outrigger so as to reposition the second portion of the bone relative to the first portion of the bone.

(71) United States Patent Application Publication Number US 2008/0195095 A1 to Renard et al.

United States Patent Application Publication Number US 2008/0195095 A1 published to Renard et al. on Aug. 14, 2008 in U.S. class 606 and subclass 54 teaches resilient external fixators between first and second bone portions. The fixator includes a helical spring having an axis, a body, first apparatus for mounting the body to co-operate with the spring so that the spring is suitable for turning relative to the body about the axis, a pin of axis suitable for being fastened on the bone, apparatus for mounting the pin to cooperate with the body so as to pass through the spring and so that the axis forms a non-zero angle with the axis, another body, and apparatus for connecting the body with the bone and the spring. The fixator is applicable specifically to external fixators for fingers.

(72) United States Patent Application Publication Number US 2008/0221571 A1 to Daluiski et al.

United States Patent Application Publication Number US 2008/0221571 A1 published to Daluiski et al. on Sep. 11, 2008 in U.S. class 606 and subclass 54 teaches an orthopedic external fixation system that may include a distal bar having a curvature that varies along its length, an uncurved proximal bar, a plurality of proximal embedding members, and a plurality of distal embedding members. The proximal and the distal embedding members, sized and shaped for embedding in bone, may attach directly or indirectly to the proximal bar and the distal bar, respectively.

(73) United States Patent Application Publication Number US 2008/0221572 A1 to Naegerl et al.

United States Patent Application Publication Number US 2008/0221572 A1 published to Naegerl et al. on Sep. 11, 2008 in U.S. class 606 and subclass 57 teaches a device for temporary fixation of parts of a human joint, which includes two holding elements disposed opposite one another and a releasable fixing device configured to fix in place a respective joint part of the human joint between the two holding elements. In addition, the device includes a support surface configured to support a distal joint part and a proximal joint part, a guide configured to position and to limit a relative movement of at least one of a surgical instrument and a surgical aid, and receiving apparatus for receiving the guide.

(74) United States Patent Application Publication Number US 2008/0221573 A1 to Kumhyr.

United States Patent Application Publication Number US 2008/0221573 A1 published to Kumhyr on Sep. 11, 2008 in U.S. class 606 and subclass 59 teaches an adjustment device for an external fixator, which has an elongated fixator body connected to bone-pin clamps at proximal and distal ends of the elongated fixator body. The adjustment device includes at least one adaptor for mounting to at least one of the bone-pin clamps. The adaptor stabilizes the bone-pins during an adjustment of the fractured bone to lessen the amount of pain experienced by a patient. An adjustment knob may be coupled to the adaptor and used to tighten or loosen a portion of the bone-pin clamp that facilitates rotation of the bone-pin clamp.

(75) United States Patent Application Publication Number US 2008/0255554 A1 to Richter et al.

United States Patent Application Publication Number US 2008/0255554 A1 published to Richter et al on Oct. 16, 2008 in U.S. class 606 and subclass 57 teaches an external fixator having a retaining member and connecting elements that can be connected, without screws, to a bone or bone parts, in particular to both halves of an opened sternum, and provide for increasing or reducing the compressive stress between the two bone parts or sternum halves.

(76) United States Patent Application Publication Number US 2008/0269741 A1 to Karidis.

United States Patent Application Publication Number US 2008/0269741 A1 published to Karidis on Oct. 30, 2008 in U.S. class 606 and subclass 56 teaches an orthopedic fixator for positioning a first element relative to a second element with controlled compliance that can be adjusted during the healing process. One embodiment includes a first frame for attachment to the first element, a second frame attached to the first frame through a plurality of adjustable effective length struts, and a third frame for attachment to the second element. The third frame is compliantly attached to the second frame. A preferred embodiment includes adjustable-length preload elements to apply unidirectional forces between the first and second frames so as preload the adjustable effective length struts and substantially reduce the positional tolerance. An alternative embodiment includes adjustable spring elements allowing the compliance of the attachment of the third frame to the second frame to be adjusted at various points in the healing process.

(77) United States Patent Application Publication Number US 2008/0281324 A1 to Webb et al.

United States Patent Application Publication Number US 2008/0281324 A1 published to Webb et al. on Nov. 13, 2008 in U.S. class 606 and subclass 59 teaches an external fixation assembly that includes a plurality of hollow pins that are inserted into a patient's bone. Each pin has an interior bore and a plurality of apertures extending through the pin wall from the bore. The pin may be coupled to a source of vacuum pressure operable to create reduced pressure in the tissue surrounding the pin. A cover is placed around the pin and sealed to provide a fluid-tight enclosure that maintains reduced pressure around the pin. A method for applying external fixation using the fixator pins includes the steps of inserting each pin through a skin opening, positioning the pin apertures near selected tissue, covering the skin opening with a sealed enclosure, connecting the pins to a source of vacuum pressure, and activating the source of vacuum pressure to create reduced pressure in the patient's tissue at or near the bone.

(78) United States Patent Application Publication Number US 2009/0018541 A1 to Lavi.

United States Patent Application Publication Number US 2009/0018541 A1 published to Lavi on Jan. 15, 2009 in U.S. class 606 and subclass 59 teaches a clamp for an external fixation system that includes a body having a bottom portion and semi-spherical top portion. The top portion has a threaded bore provided along a longitudinal axis. The clamp includes a clamp assembly having a base with a semi-spherical cavity and a lid positioned over the base to house at least one pin between the base and the lid. The base and the lid have a bore provided along a longitudinal axis thereof. A fastening member extends through the bore in the base and the lid of the clamp assembly and is secured within the threaded bore of the top portion of the body. The bores in the base and the lid have a diameter that is greater than the diameter of the fastening member.

(79) United States Patent Application Publication Number US 2009/0024128 A1 to Nakamura et al.

United States Patent Application Publication Number US 2009/0024128 A1 published to Nakamura et al. on Jan. 22, 2009 in U.S. class 606 and subclass 54 teaches an external skeletal fixation device that reduces load on the patient, is capable of freely moving, and deformity correction of a bone and bone fragments. The external skeletal fixation device includes a pair of pin clamp units fixedly holding rodlike members inserted, respectively, into a first part and a second part of a bone on the opposite sides, respectively, of a virtual hinge point in the bone. The virtual hinge point corresponds to a center of rotational angulation of the bone, a center on which the first and the second part of the bone, respectively, on the opposite sides of a fracture site of the bone or a part of the osteotomy site for deformity correction are turned, or a center about which a joint turns. A connecting mechanism connecting the pair of pin clamp units has a pair of arms pivotally connected to the pair of pin clamp units, respectively. The pair of arms are pivotally joined together. The respective axes of rotary joints, respectively, connect the pin clamp units and the arm, and the arms extend toward the virtual hinge point.

(80) United States Patent Application Publication Number US 2009/0036889 A1 to Callender.

United States Patent Application Publication Number US 2009/0036889 A1 published to Callender on Feb. 5, 2009 in U.S. class 606 and subclass 55 teaches a method and apparatus for treatment of sleep apnea, which employs bone screws implanted into a patient's anterior maxillary bone above and posterior to the cuspids, and posterior mandibular bone below and between any of the posterior teeth. Elastics are stretched between the maxillary and mandibular bone screws to exert forces to bias the mandible forward with respect to the maxilla. An aligner can be placed between the patient's upper and lower to help maintain proper positioning of the mandible.

(81) United States Patent Application Publication Number US 2009/0036891 A1 to Brown et al.

United States Patent Application Publication Number US 2009/0036891 A1 published to Brown et al. on Feb. 5, 2009 in U.S. class 606 and subclass 57 teaches an orthopaedic fixation clamp for use in an external fixation system and its method of use.

(82) United States Patent Application Publication Number US 2009/0088751 A1 to Mullaney.

United States Patent Application Publication Number US 2009/0088751 A1 published to Mullaney on Apr. 2, 2009 in U.S. class 606 and subclass 59 teaches clamping devices and methods for external fixation systems, which include a post component having a yaw axis, and a clamping system secured to the post component and rotatable about the yaw axis. The clamping system includes an outer jaw and an inner jaw having an inner surface facing the outer jaw. The outer and inner jaws together form an opening for receiving a fixation element of the external fixation system. The inner jaw and outer jaw have a roll axis alignable with a longitudinal axis of the fixation element. The clamping system and post component are rotatable about the roll axis. The inner jaw also includes a cylindrical outer-facing surface. The devices also include a base component having a cylindrical concave surface having a pitch axis. The concave surface of the base component interfaces with the cylindrical outer facing component on the inner jaw. The outer and inner jaws are rotatable relative to the base and the post component about the pitch axis.

(83) United States Patent Application Publication Number US 2009/0099565 A1 to Weiner et al.

United States Patent Application Publication Number US 2009/0099565 A1 published to Weiner et al. on Apr. 16, 2009 in U.S. class 606 and subclass 54 teaches an external fixator that includes a main body and an outrigger for extending over a fractured joint, such as a wrist joint. The main body can be positioned next to a right arm or flipped over and positioned next to a left arm. The outrigger is attachable to extend either to the left or to the right of the main body, as appropriate. A distal body is removably connectable to the distal end of the main body and can be affixed to bone on the opposite side of the fracture to immobilize the joint where the fracture occurs. The distal body is connected to the main body with an adjustable securement section that provides six degrees of adjustment freedom. The outrigger is attached to the main body through a slide plate in a dual rail configuration that provides two dimensions of adjustment. Fragment pin supports ride in a track of the outrigger and provide seven degrees of adjustment freedom for directed fixation of fragments at the fracture site. The outrigger is pivotally adjustable relative to the main body and includes track portions separated by a wrap around angle. The major components of the fixator are molded of plastic. A surgical technique using the fixator includes immobilizing the joint for an initial healing duration and retaining fragment pins in place during a secondary healing duration.

It is apparent that numerous innovations for fixators have been provided in the prior art, which are adapted to be used. Furthermore, even though these innovations may be suitable for the specific individual purposes to which they address, however, they would not be suitable for the purposes of the embodiments of the present invention as heretofore described.

2. SUMMARY OF THE INVENTION

Thus, an object of the embodiments of the present invention is to provide a dynamic external fixator, which avoids disadvantages of the prior art.

Briefly stated, another object of the embodiments of the present invention is to provide an orthopedic apparatus for bridging between a first bone unit and a second bone unit of at least one of an injured bone and/or of an injured joint for one of distraction, compression, static placement and/or relative rotation of the at least one of the bones and the joint, and method of implanting and/or using the apparatus. The apparatus includes a first attaching apparatus, a second attaching apparatus, and a control apparatus. The first attaching apparatus connects the apparatus to the first bone unit. The second attaching apparatus connects the apparatus to the second bone unit. The control apparatus is operatively associated with the first attaching apparatus and with the second attaching apparatus to produce at least two conditions. In a first of the conditions, the second bone unit is urged in a first direction relative to the first bone unit for one of the distraction and the compression of the at least one of the bones and/or providing controlled rotation of the joint. In a second of the conditions, the second bone unit is urged in a direction other than the first direction for the distraction and the compression of the at least one of the bones and/or joint. The control apparatus can also provide for control of relative rotation of the joint. The control apparatus preferably includes a reformably deformable member that positions the first attaching apparatus and the second attaching apparatus in juxtaposed orientation relative to each other.

The novel features considered characteristic of the embodiments of the present invention are set forth in the appended claims. The embodiments of the present invention themselves, however, both as to their construction and their method of operation together with additional objects and advantages thereof will be best understood from the following description of the specific embodiments when read and understood in connection with the accompanying drawing.

3. BRIEF DESCRIPTION OF THE DRAWING

The figures of the drawing are briefly described as follows:

FIG. 1 is a diagrammatic side elevational view of the prior art distraction apparatus taught by U.S. Pat. No. 5,074,865 to Fahmy;

4. LIST OF REFERENCE NUMERALS UTILIZED IN THE DRAWING

Figure 1:
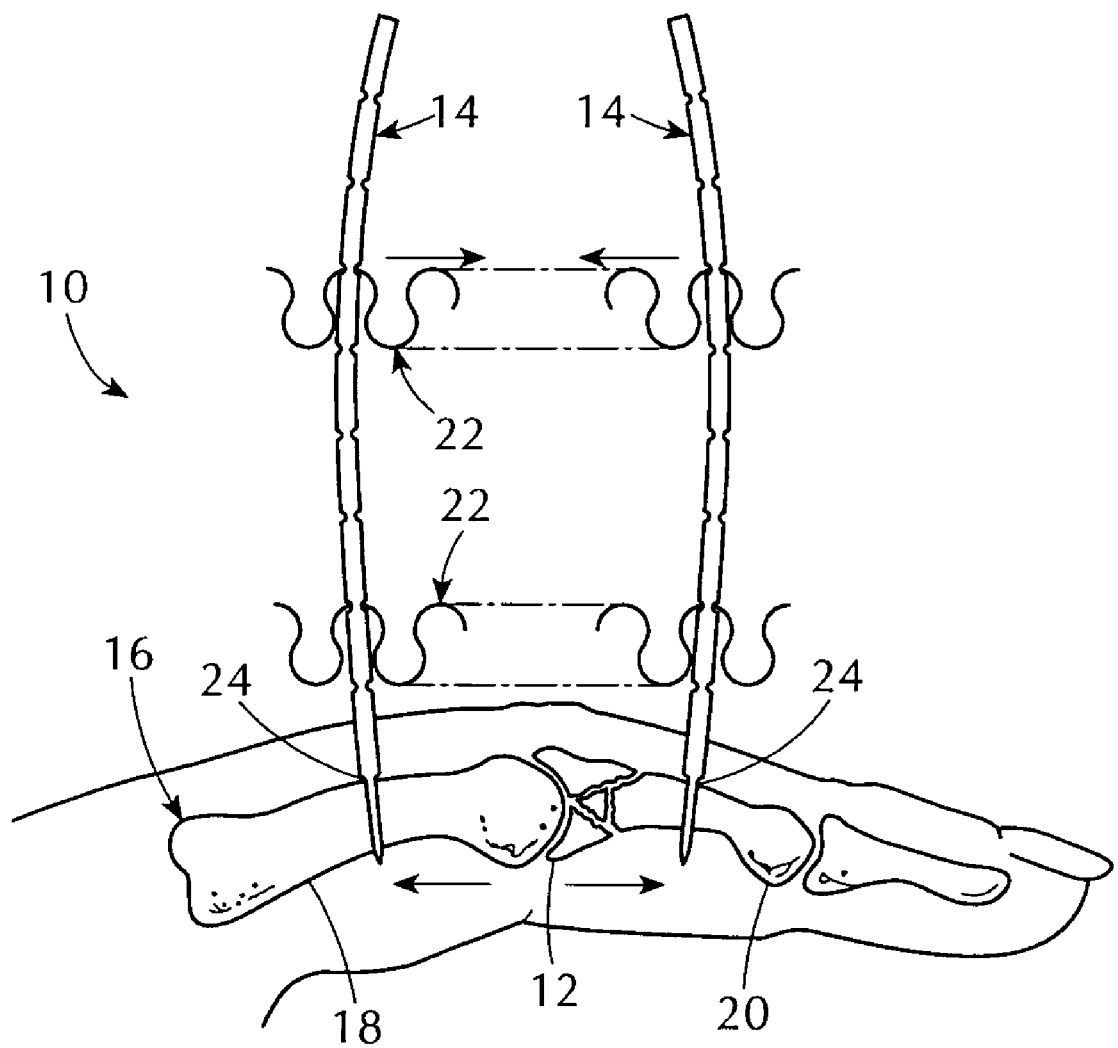

A Prior art.
10 distraction apparatus for maintaining fractured joint 12 during healing
12 fractured joint
14 pair of pins for insertion into bone 16 at positions proximal to 18 and distal to 20 fractured joint 12

16 bone
18 position proximal to fractured joint 12
20 position distal to fractured joint 12
22 pair of stainless steel wire springs
24 pin insertions into bone 16
B. General.
30 orthopedic apparatus of embodiments of present invention for bridging between first bone unit 32 and second bone unit 34 of at least one of injured bone 36 and injured joint 38 for one of distraction (direction of ARROWS 40), compression (direction of ARROWS 42), static positioning and/or control range or rotational motion of at least one of the bones 36 and/or joint 38
32 first bone unit
34 second bone unit
36 injured bone
38 injured joint
40 direction of ARROWS of distraction
42 direction of ARROWS of compression
C. Overall configuration of orthopedic apparatus 30.
44 first attaching apparatus for connecting apparatus 30 to first bone unit 32
46 second attaching apparatus for connecting apparatus 30 to second bone unit 34
48 control apparatus
50 reformably deformable member of control apparatus 48 that moves first attaching apparatus 44 and second attaching apparatus 46 relative to each other
D. Specific configuration of first attaching apparatus 44.
52 at least one first generally circular-shaped ring of first attaching apparatus 44 for receiving end 54 of at least one first pin 56, respectively, passing transversely at least into first bone unit 32
54 end of at least one first pin 56 passing transversely at least into first bone unit 32
56 at least one first pin passing transversely at least into first bone unit 32
58 direction of ARROWS of flexion and extension
62 center of rotation of head 64 of first bone unit 32
64 head of first bone unit 32
E. Specific configuration of second attaching apparatus 46.
66 at least one second generally circular-shaped ring of second attaching apparatus 46 for receiving end 68 of at least one second pin 70, respectively, passing transversely at least into second bone unit 34
68 end of at least one second pin 70 passing transversely at least into second bone unit 34
70 at least one second pin passing transversely at least into second bone unit 34
78 rod of at least a pair of second generally circular-shaped rings 66 of second attaching apparatus 46
80 one side of at least one of injured bone 36 and injured joint 38
82 other side of at least one of injured bone 36 and injured joint 38
84 other end of at least one first pin 56
86 other end of at least one second pin 76
F. Specific configuration of control apparatus 48.
88 generally rhombus-shaped ring of control apparatus 48
90 forward angle of generally rhombus-shaped ring 88 of control apparatus 48
92 rearward angle of generally rhombus-shaped ring 88 of control apparatus 48
94 top angle of generally rhombus-shaped ring 88 of control apparatus 48
96 bottom angle of generally rhombus-shaped ring 88 of control apparatus 48

5. DETAILED DESCRIPTION OF THE PREFERRED EMBODIMENTS

A. General.

Figure 2:
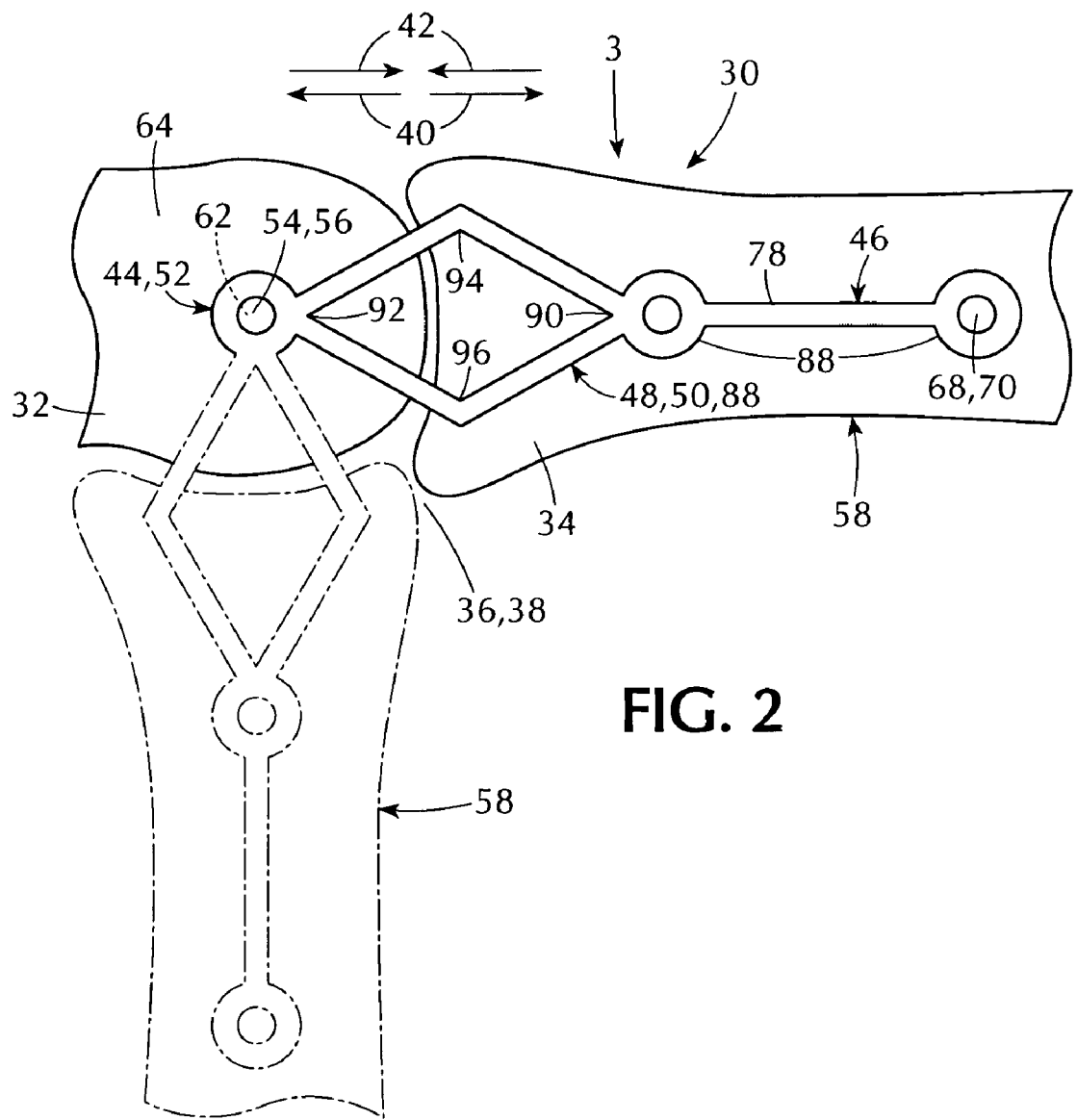
FIG. 2 is a diagrammatic elevational view of the orthopedic external fixator of the embodiments of the present invention.
Figure 3:
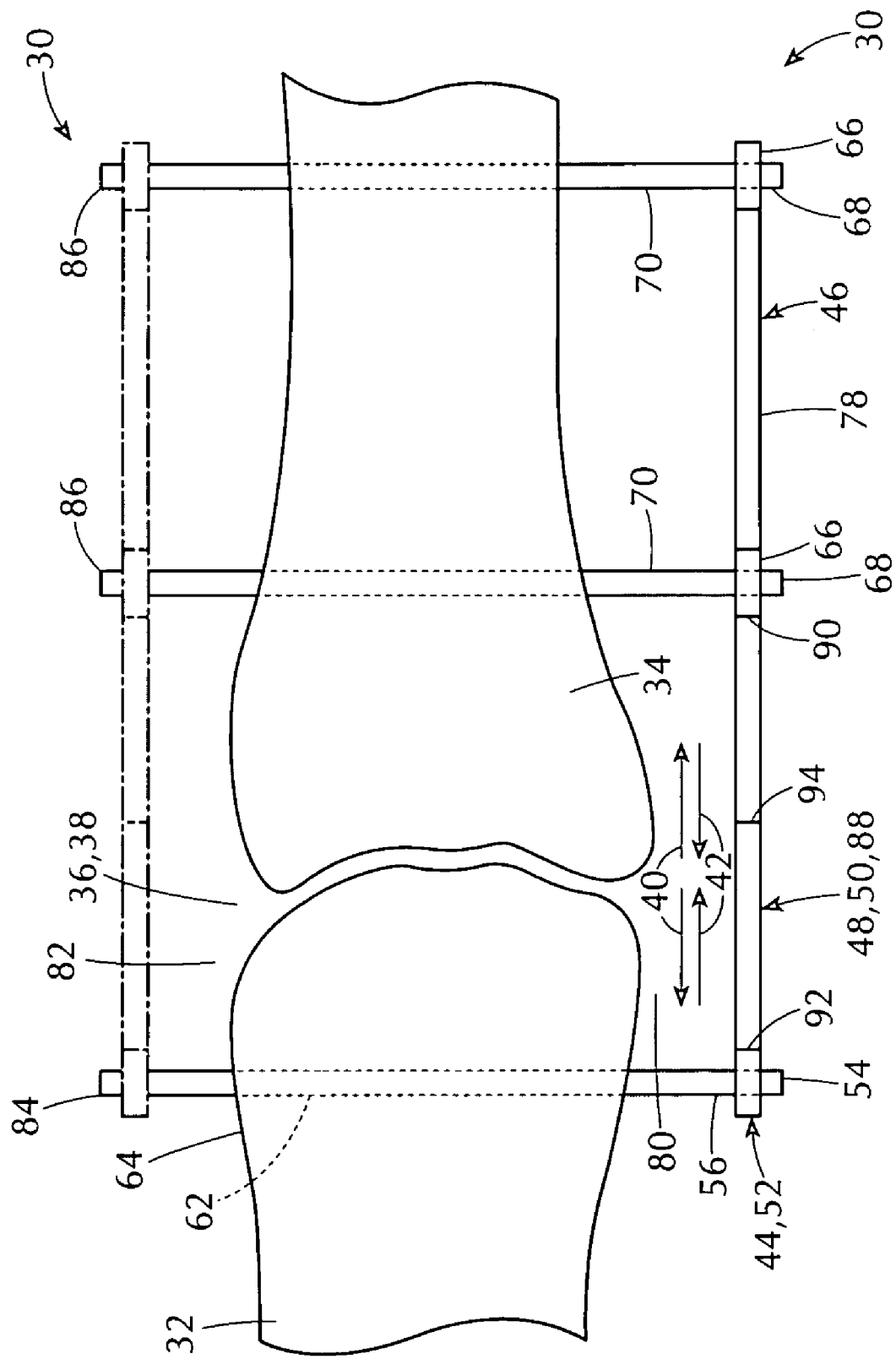
FIG. 3 is a diagrammatic top plan view taken generally in the direction of ARROW 3 in FIG. 2.

Referring now to the figures, in which like numerals indicate like parts, and more particularly to FIGS. 2 and 3, which are, respectively, a diagrammatic elevational view of the external fixator of the embodiments of the present invention, and a diagrammatic top plan view taken generally in the direction of ARROW 3 in FIG. 2, the orthopedic apparatus of the embodiments of the present invention is shown generally at 30 for bridging between a first bone unit 32 and a second bone unit 34 of at least one being an injured bone 36 and/or an injured joint 38 for one of distraction (direction of ARROWS 40), compression (direction of ARROWS 42), static position, and control of range of relative rotary motion of the at least one of the bones 36 and the joint 38.

B. The Overall Configuration of the Orthopedic Apparatus 30.

The orthopedic apparatus 30 comprises a first attaching apparatus 44, a second attaching apparatus 46, and a control apparatus 48. The first attaching apparatus 44 is for connecting the apparatus 30 to the first bone unit 32. The second attaching apparatus 46 is for connecting the apparatus 30 to the second bone unit 34. The control apparatus 48 is operatively associated with the first attaching apparatus 44 and with the second attaching apparatus 46 to produce at least two conditions. In a first of the conditions, the second bone unit 34 is urged in a first direction relative to the first bone unit 32 for one of the distraction (ARROWS 40) and the compression (ARROWS 42) of the at least one of the injured bone 36 and the injured joint 38. In a second of the conditions, the second bone unit 34 is translated and/or rotated in a direction other than the first direction for the other one of the distraction (ARROWS 40) and the compression (ARROWS 42) of the at least one of the injured bone 36 and/or the injured joint 38. The control apparatus 48 includes a reformally deformable member 50 that moves the first attaching apparatus 44 and the second attaching apparatus 46 relative to each other.

The apparatus 30 is made from a material selected from the group consisting of stainless steel, aluminum, and brass.

C. The Specific Configuration of the First Attaching Apparatus 44.

The first attaching apparatus 44 includes at least one first generally circular-shaped ring 52. The at least one first generally circular-shaped ring 52 of the first attaching apparatus 44 is for receiving an end 54 of at least one first pin 56, respectively, passing transversely at least into the first bone unit 32.

The at least one first pin 56 is selected from the group consisting of a K-wire and a rod, each having a diameter in a range of 0.045-0.062 inches.

The at least one first pin 56 is for passing transversely at least into the center of rotation 62 of the head 64 of the first bone unit 32 so as to allow the second bone unit 34 to rotate by flexion and extension (direction of ARROWS 58) by allowing the apparatus 30 to pivot around the at least one first pin 56 when the at least one first pin 56 is one first pin 56.

D. The Specific Configuration of the Second Attaching Apparatus 46.

The second attaching apparatus 46 includes at least one second generally circular-shaped ring 66. The at least one second generally circular-shaped ring 66 of the second attaching apparatus 46 is for receiving an end 68 of at least one second pin 70, respectively, passing transversely at least into the second bone unit 34.

The at least one second pin 70 is selected from the group consisting of a K-wire and a rod, each having a diameter in a range of 0.045-0.062 inches.

The at least one second generally circular-shaped ring 66 of the second attaching apparatus 46 is at least a pair of second generally circular-shaped rings 66. The at least one pair of second generally circular-shaped rings 66 of the second attaching apparatus 46 receives at least a pair of second pins 70, respectively.

The at least one pair of second generally circular-shaped rings 66 of the second attaching apparatus 46 are connected to each other by a rod 78.

As shown in FIG. 3, the apparatus 30 is for positioning on one side 80 of the at least one of the injured bone 36 and the injured joint 38. Another apparatus 30 is for positioning on the other side 82 of the at least one of the injured bone 36 and the injured joint 38 and receives the other end 84 of the at least one first pin 56, respectively, and the other end 86 of the at least one second pin 70, respectively.

E. The Specific Configuration of the Control Apparatus 48.

The control apparatus 48 includes a generally rhombus-shaped ring 88. The generally rhombus-shaped ring 88 of the control apparatus 48 is straddled by the at least one first generally circular-shaped ring 52 of the first attaching apparatus 44 and the at least one second generally circular-shaped ring 66 of the second attaching apparatus 46.

The generally rhombus-shaped ring 88 of the control apparatus 48 has a forward angle 90 and a rearward angle 92. The at least one second generally circular-shaped ring 66 of the second attaching apparatus 46 extends forwardly from the forward angle 90 of the generally rhombus-shaped ring 88 of the control apparatus 48. The at least one first generally circular-shaped ring 52 of the first attaching apparatus 44 extends rearwardly from the rearward angle 92 of the generally rhombus-shaped ring 88 of the control apparatus 48.

The generally rhombus-shaped ring 88 of the control apparatus 48 has a top angle 94 and a bottom angle 96. The top angle 94 of the generally rhombus-shaped ring 88 of the control apparatus 48 and the bottom angle 96 of the generally rhombus-shaped ring 88 of the control apparatus 48 when moved cause the generally rhombus-shaped ring 88 of the control apparatus 48 to deform and move the first attaching apparatus 44 and the second attaching apparatus 46 relative to each other, and in doing so, moves the first bone unit 32 and the second bone unit 34 relative to each other.

The generally rhombus-shaped ring 88 of the control apparatus 48 is made from a non-memory metal so as to allow it to maintain its deformed shape once deformed, and is deformed to move the first attaching apparatus 44 and the second attaching apparatus 46 relative to each other in a range of 1-3 mm.

F. The Method for Using the Orthopedic Apparatus 30 for Bridging Between the First Bone Unit 32 and the Second Bone Unit 34 of the at Least One of the Injured Bone 36 and the Injured Joint 38 for One of the Distraction, the Compression, the Static Positioning and/or Control of Range of Relative Rotary Motion of the at Least One of the Bones 36 and/or the Joint 38.

Figure 4A:
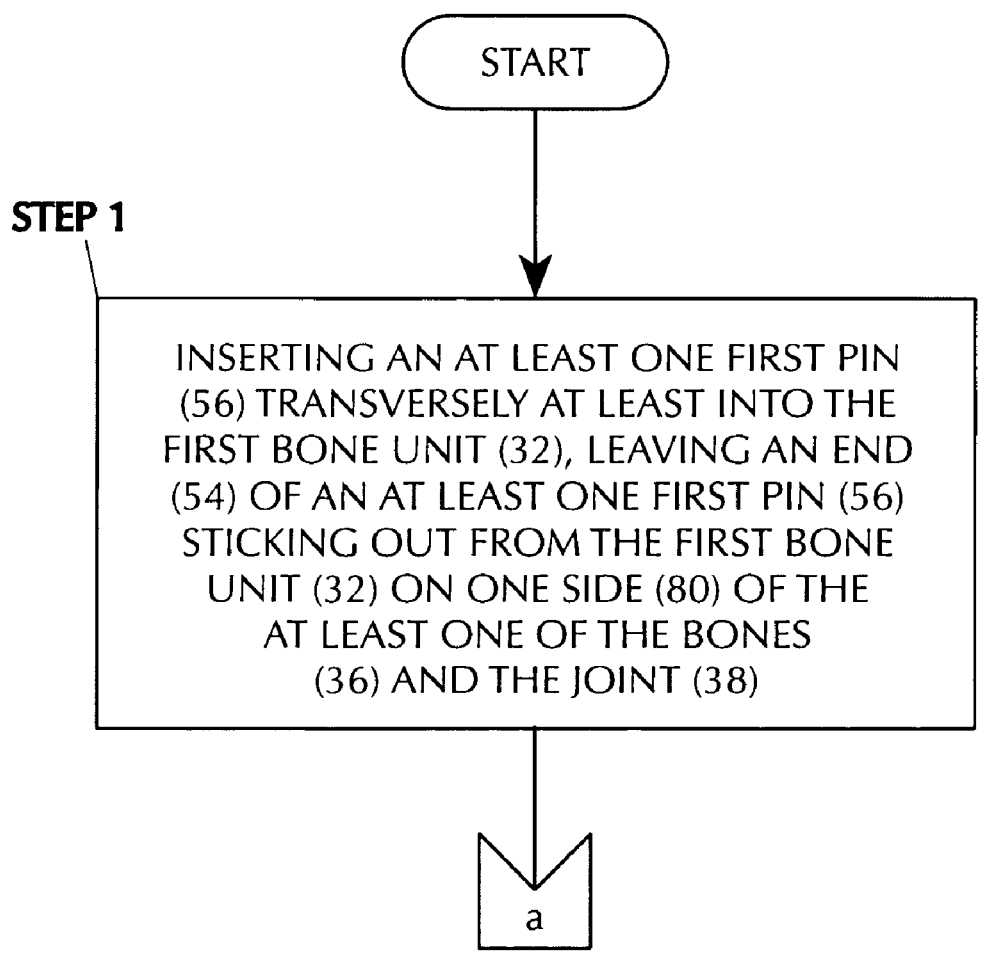
FIGS. 4A-4D are a flowchart of the method for using an orthopedic apparatus for bridging between a first bone unit and a second bone unit.
Figure 4B:
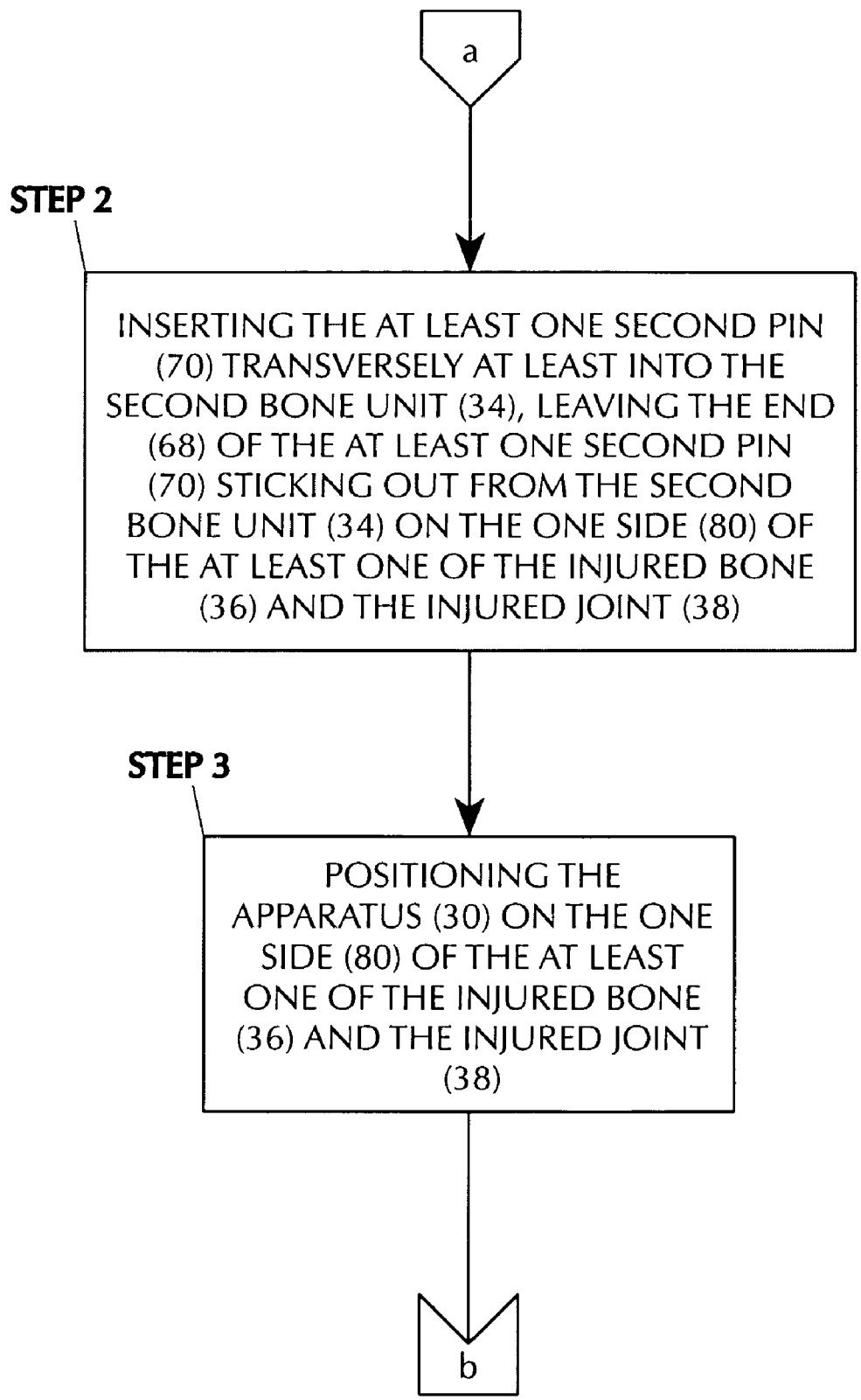
Figure 4C:
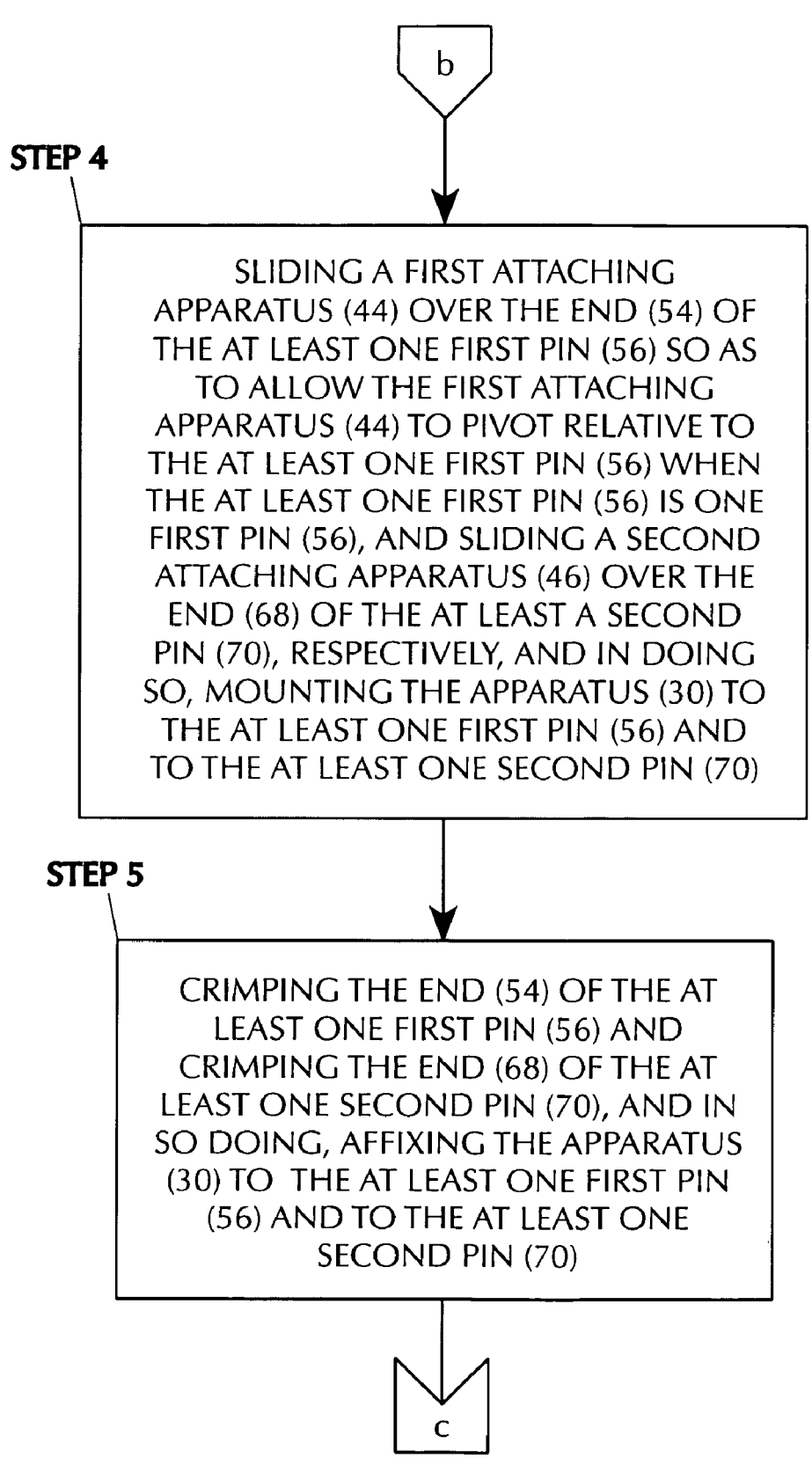
Figure 4D:
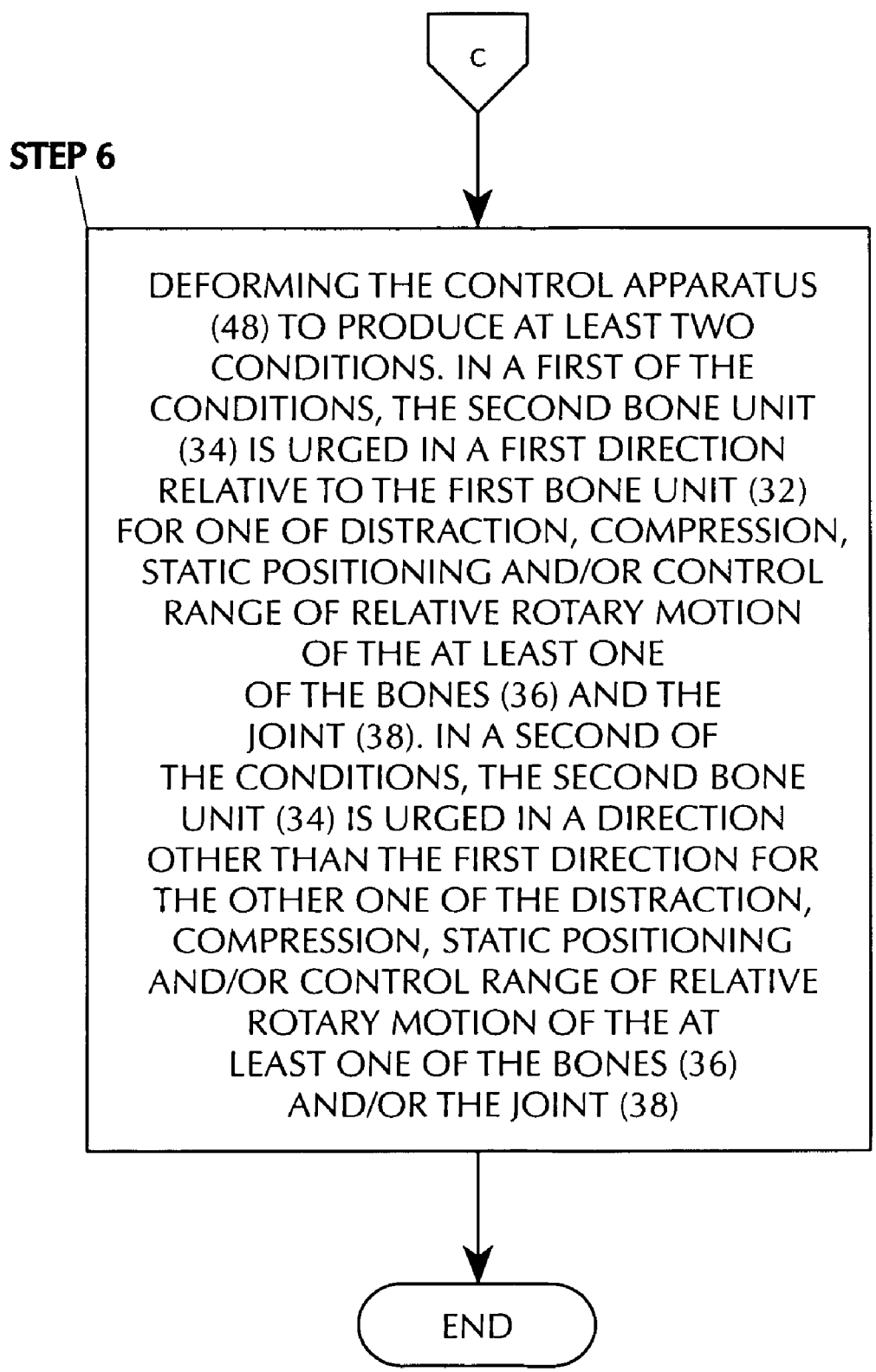

The method for using the orthopedic apparatus 30 for bridging between the first bone unit 32 and the second bone unit 34 of the at least one of the bones 36 and/or the joint 38 for one of the distraction, the compression, the static positioning and/or control of range of relative motion of the at least one of the bones 36 and/or the joint 38 can best be seen in FIGS. 4A-4ZZ, which are a flowchart of the method for using an orthopedic apparatus for bridging between a first bone unit and a second bone unit, and as such, will be discussed with reference thereto.

The method for using the orthopedic apparatus 30 for bridging between the first bone unit 32 and the second bone unit 34 of the at least one of the bones 36 and/or the joint 38 for one of the distraction, the compression, the static positioning and/or the control of range or relative motion of the at least one of the bones 36 and the joint 38 comprises the steps of:

STEP 1: Inserting the at least one first pin 56 transversely at least into the first bone unit 32, leaving the end 54 of the at least one first pin 56 sticking out from the first bone unit 32 on the one side 80 of the at least one of the bones 36 and/or the joint 38.

STEP 2: Inserting the at least one second pin 70 transversely at least into the second bone unit 34, leaving the end 68 of the at least one second pin 70 sticking out from the second bone unit 34 on the one side 80 of at the least one of the bones 36 and the joint 38.

STEP 3: Positioning the apparatus 30 on the one side 80 of the at least one of the bones 36 and the joint 38.

STEP 4: Sliding the first attaching apparatus 44 over the end 54 of the at least one first pin 56 so as to allow the first attaching apparatus 44 to pivot relative to the at least one first pin 56 when the at least one first pin 56 is one first pin 56, and sliding the second attaching apparatus 46 over the end 68 of the at least one second pin 70, respectively, and in doing so, mounting the apparatus 30 to the at least one first pin 56 and to the at least one second pin 70.

STEP 5: Crimping the end 54 of the at least one first pin 56 and crimping the end 68 of the at least one second pin 70, and in so doing, affixing the apparatus 30 to the at least one first pin 56 and to the at least one second pin 70.

STEP 6: Deforming the control apparatus 48 to produce at least two conditions. In a first of the conditions, the second bone unit 34 is urged in a first direction relative to the first bone unit 32 for one of the distraction, the compression, the static positioning and/or the control of range or relative rotary motion of the at least one of the bones 36 and/or the joint 38. In a second of the conditions, the second bone unit 34 is urged in a direction other than the first direction for the other one of the distraction, the compression, the static positioning and/or the control of range or relative rotary motion of the at least one of the bones 36 and the joint 38.

G. The Impressions.

It will be understood that each of the elements described above or two or more together may also find a useful application in other types of constructions differing from the types described above.

While the embodiments of the present invention have been illustrated and described as embodied in a orthopedic external fixator and method of use, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. An orthopedic apparatus for bridging between a first bone unit and a second bone unit of at least one of an injured bone and an injured joint for one of distraction, compression, and static of the at least one of the injured bone and the injured joint, comprising:

a) first attaching means for connecting said apparatus to the first bone unit;
b) second attaching means for connecting said apparatus to the second bone unit; and
c) control means operatively associated with said first attaching means and with said second attaching means to produce at least two conditions:
   I) in a first of said conditions, the second bone unit is urged in a first direction relative to the first bone unit for one of the distraction and the compression of the at least one of the injured bone and the injured joint, and
   ii) in a second of said conditions, the second bone unit is urged in a direction other than said first direction for the other one of the distraction and the compression of the at least one of the injured bone and the injured joint;
wherein said control means includes a reformally deformable member that moves said first attaching means and said second attaching means relative to each other;
wherein said first attaching means includes at least one first circular-shaped ring;
wherein said at least one first circular-shaped ring of said first attaching means is for receiving an end of at least one first pin, respectively, passing transversely at least into the first bone unit;
wherein said second attaching means includes at least one second circular-shaped ring;
wherein said at least one second circular-shaped ring of said second attaching means is for receiving an end of at least one second pin, respectively, passing transversely at least into the second bone unit;
wherein said at least one second circular-shaped ring of said second attaching means is at least a pair of second circular-shaped rings;
wherein said at least a pair of second circular-shaped rings of said second attaching means receive at least a pair of second pins, respectively;
wherein said at least a pair of second circular-shaped rings of said second attaching means are connected to each other by a rod;
wherein said control means is connected between said at least one first circular-shaped ring of said first attaching means and said at least one second circular-shaped ring of said second attaching means;
wherein said control means includes a rhombus-shaped ring; and
wherein said rhombus-shaped ring of said control means is made from a non-memory metal so as to allow it to maintain its deformed shape once deformed.

2. The apparatus of claim 1, wherein said rhombus-shaped ring of said control means is straddled by said at least one first circular-shaped ring of said first attaching means and said at least one second circular-shaped ring of said second attaching means.

3. The apparatus of claim 2, wherein said rhombus-shaped ring of said control means has:

a) a top angle; and
b) a bottom angle;
wherein said top angle of said rhombus-shaped ring of said control means and said bottom angle of said rhombus-shaped ring of said control means when moved cause said rhombus-shaped ring of said control means to deform and move said first attaching means and said second attaching means relative to each other, and in doing so, moves the first bone unit and the second bone unit relative to each other.

4. The apparatus of claim 3, wherein said rhombus-shaped ring of said control means is deformed to move said first attaching means and said second attaching means relative to each other in a range of 1-3 mm.

5. The apparatus of claim 2, wherein said rhombus-shaped ring of said control means has:

a) a forward angle; and
b) a rearward angle;
wherein said at least one second circular-shaped ring of said second attaching means extends forwardly from said forward angle of said rhombus-shaped ring of said control means; and
wherein said at least one first circular-shaped ring of said first attaching means extends rearwardly from said rearward angle of said rhombus-shaped ring of said control means.

6. The apparatus of claim 1, wherein said at least one first pin is selected from the group consisting of a K-wire and a rod.

7. The apparatus of claim 6, wherein said at least one first pin is selected from the group consisting of a K-wire and a rod, each having a diameter in a range of 0.045-0.062 inches.

8. The apparatus of claim 1, wherein said at least one second pin is selected from the group consisting of a K-wire and a rod.

9. The apparatus of claim 8, wherein said at least one second pin is selected from the group consisting of a K-wire and a rod, each having a diameter in a range of 0.045-0.062 inches.

10. The apparatus of claim 1, wherein said apparatus is made from a material selected from the group consisting of stainless steel, aluminum, and brass.

11. The apparatus of claim 1, wherein said at least one first pin is for passing transversely at least into the center of rotation of the head of the first bone unit so as to allow the second bone unit to rotate by flexion and extension by allowing said apparatus to pivot around said at least one first pin when said at least one first pin is one first pin.

12. The apparatus of claim 1, wherein said apparatus is for positioning on one side of the at least one of the injured bone and the injured joint; and
wherein another said apparatus is for positioning on the other side of the at least one of the injured bone and the injured joint and receives the other end of the at least one first pin, respectively, and the other end of the at least one second pin, respectively.

* * * * *